(12) United States Patent
Gualtieri et al.

(10) Patent No.: US 12,327,208 B2
(45) Date of Patent: Jun. 10, 2025

(54) SYSTEMS AND METHODS FOR IMPROVED INTERRUPTION AND RESUMPTION MANAGEMENT

(71) Applicant: GE Precision Healthcare LLC, Wauwatosa, WI (US)

(72) Inventors: James Gualtieri, Glenshaw, PA (US); Ann Trumble, Mequon, WI (US); Sean P. O'Connor, San Francisco, CA (US); Audrey Clarke, Chicago, IL (US)

(73) Assignee: General Electric Company, Schenectady, NY (US)

( * ) Notice: Subject to any disclaimer, the term of this patent is extended or adjusted under 35 U.S.C. 154(b) by 679 days.

(21) Appl. No.: 17/490,398

(22) Filed: Sep. 30, 2021

(65) Prior Publication Data
US 2023/0101589 A1  Mar. 30, 2023

(51) Int. Cl.
*G06Q 10/0631* (2023.01)
*G06F 18/25* (2023.01)
*G06Q 10/0633* (2023.01)

(52) U.S. Cl.
CPC ..... *G06Q 10/06316* (2013.01); *G06F 18/256* (2023.01); *G06Q 10/063114* (2013.01); *G06Q 10/0633* (2013.01)

(58) Field of Classification Search
None
See application file for complete search history.

(56) References Cited

U.S. PATENT DOCUMENTS

2009/0147940 A1* 6/2009 Graves .............. H04M 3/42365
                                                     379/208.01
2019/0340014 A1* 11/2019 Fishel ...................... G06N 3/08

FOREIGN PATENT DOCUMENTS

WO  WO-2022139795 A1 *  6/2022  .......... G06F 9/4881

OTHER PUBLICATIONS

Sloane, J.F., Donkin, C., Newell, B.R. et al. Managing Interruptions to Improve Diagnostic Decision-Making: Strategies and Recommended Research Agenda.2023, J Gen Intern Med vol. 38, pp. 1526-1531 (Year: 2023).*
International Application No. PCT/US2022/045185 filed Sep. 29, 2022—International Search Report and Written Opinion issued on Mar. 3, 2023; 16 pages.

* cited by examiner

*Primary Examiner* — Amanda Gurski

(57) ABSTRACT

Interruptions of user activity can cost time and money for organizations. Improved technology is needed for interruption and resumption management. A communication engine can monitor the task state of a user, receive an incoming matter, analyze the incoming matter with a classification model, compare the analyzed incoming matter with the priority of the task state of the user, and interrupt the user by providing the incoming matter to the user if the priority of the analyzed incoming matter is greater than the priority of the task state of the user. When the user would like to resume their interrupted task, the communication engine can provide an output refocus communication and automatically return the device software status to the task state of the user when the interruption occurred.

18 Claims, 19 Drawing Sheets

SYSTEMS AND METHODS FOR IMPROVED INTERRUPTION AND RESUMPTION MANAGEMENT

TECHNICAL FIELD

The subject matter disclosed herein relates generally to hardware and software computer technology that improves the digital dispatching of communications, decision support for user interruptions, and provision of user support when resuming computer tasks.

BACKGROUND

Interruptions are a problem in the healthcare industry. These are digital and physical matters that interrupt a physician, clinician, nurse, radiologist, or other healthcare professional. Each interruption can break the focus of the individual, taking time and disrupting focus. Interruptions can lead individuals to make mistakes or errors, costing time, money, and potentially the health of patients. Interruptions of individuals who run healthcare machines (like medical scanning devices) can cost hospitals money in not completing the necessary scans for the day and/or causing operational failures. Studies have shown that interruptions for medical professionals can have negative impacts on safety and patient outcomes. Interruptions during reading radiology reports can also have negative outcomes if errors are made in diagnosis or the full analysis is not provided because an interruption led to a radiologist forgetting a key observation in their train of thought.

Radiologists may waste a large amount of time each day switching between diagnostic task work and external communications. This waste is not from the actual response to the communication, but from the cognitive cost associated with switching from one task to another. Medical professionals can lose an hour each day to interruptions in their process, sometimes resulting in errors in diagnosis. Communication engines are proposed herein to improve the interruption management, provide automated responses without interrupting the user, and priority setting for interruption flow. Communication engines may also be called 'comms engines' in this specification.

Further, improved technology is needed to help individuals when they are resuming their tasks after an interruption. The faster an individual can get back into the focused state, the faster the task will be concluded and with better results. Technological systems and methods for improved interruption handling and task resumption are proposed herein.

BRIEF DESCRIPTION

In accordance with an embodiment, a communication engine is provided that can monitor the task state of a user; receive an incoming matter; analyze the incoming matter with a classification model; compare the analyzed incoming matter with the priority of the task state of the user; and interrupt the user by providing the incoming matter to the user if the priority of the analyzed incoming matter is greater than the priority of the task state of the user. The communication engine may consider if the priority of the task state of the user is greater than the priority of the incoming matter, the incoming matter is recorded and saved to be provided to the user at a future time. The communication also may specify that the future time when the incoming matter is provided to the user is when the has a lull in task activity as identified by an activity model. In the communication engine, the comparison of the analyzed incoming matter with the priority of the task state of the user also compares the incoming matter with the priority of the upcoming tasks of the user from a worklist manager for the user.

The communication engine may, after the compare step: determine as to whether the communication engine can provide an automated response to an originator of the incoming matter based on the output of the classification model; pull data from an information storage in response to the incoming matter; customize an output response based on the originator details and including the pulled data; and provide the automated output response to the originator of the incoming matter without user interruption.

The communication engine further provides that wherein if the priority of the incoming matter is higher than the priority of the task state of the user and the user is interrupted by the incoming matter, the device is further caused to: save the task state of the user; save the task context of the user; prepare an output refocus communication for when the user resumes the interrupted task; and when the user resumes the interrupted task, provide the output refocus communication and automatically return the device software status to the task state of the user when the interruption occurred.

The communication engine may also improve based on feedback and monitoring of its activity. The communication engine may collect task performance metrics and outcomes and provides the task performance metrics and outcomes to a learning engine to improve the classification model and prioritization comparison. The communication may also receive direct input from a user as to their preferences and feedback, and adjust the prioritization comparison in the future based on the direct input from a user.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized, and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Figure 1:
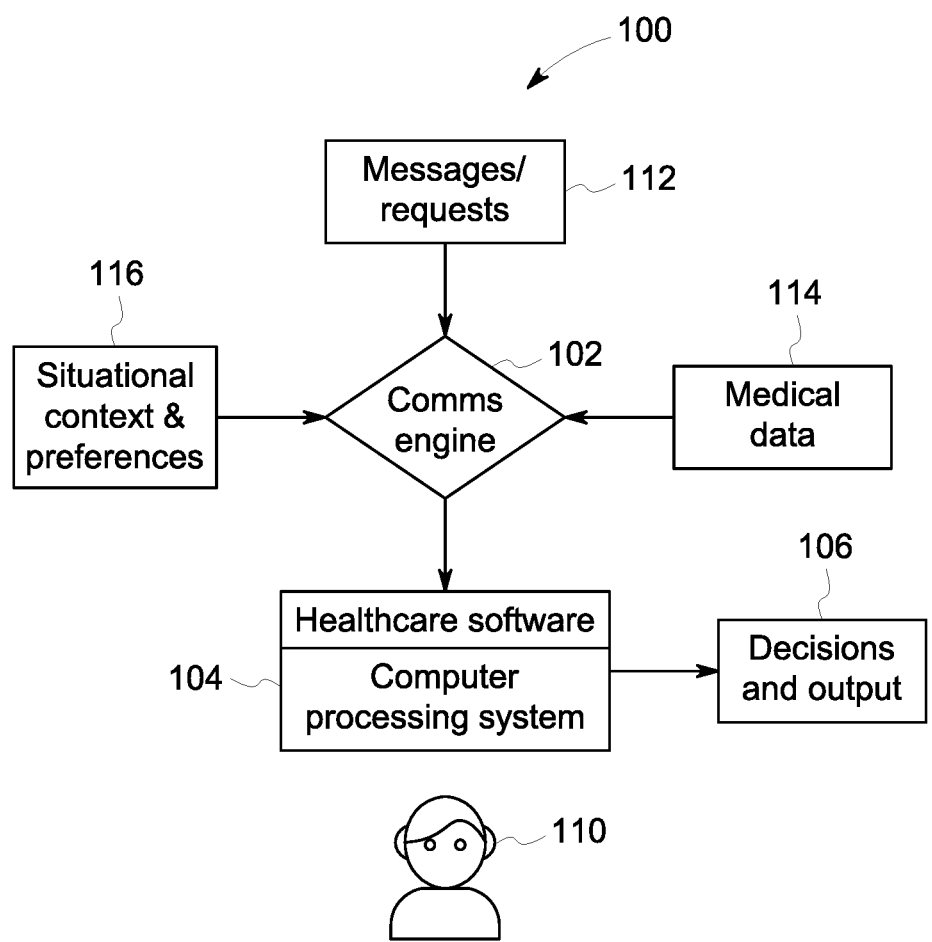
FIG. 1 shows a system in an interconnected medical environment including a communication engine, according to an embodiment.

FIG. 1 shows a system in an interconnected medical environment including a communication engine, according to an embodiment. FIG. 1 includes a healthcare ecosystem 100, messages or requests 112 (also known as incoming matters), comms engine 102, situational context and preferences 116, medical data 114, computer processing system 104 with healthcare software, decisions and output 106, and user 110. User 110 is an individual who may be a healthcare provider, clinician, physician, radiologist, nurse, or other role in a medical healthcare environment.

User 110 uses computer processing system 104 (such as a smart phone, tablet computer, or desktop computer) to help solve medical issues for patients, leading to healthcare decisions and outputs 106. Users 110 may waste time each day switching between diagnostic task work and external communications. Comms engine 102 is a machine learning (ML) or artificial intelligence enabled engine that monitors incoming matters 112 across multiple communication channels and serves to automate and control the sending of messages to limit their impact on user 110 work tasks. In addition, comms engine 102 is editable by user 110 so that they can direct activities and priorities and coordinate the user-algorithm team response.

Comms engine 102 provides workflow efficiency by analyzing incoming matters 112 such as message and requests. Comms engine 102 can also monitor the situation of user 110 including their current activity, where they are looking, their preferences, and which types of incoming matters 112 are most relevant to the current situation user 110 may be in. For example, if an incoming matter 112 is a phone call from a doctor calling about the specific patient or report (from medical data 114) that the user 110, in this example a radiologist, is working on, then comms engine 102 will likely allow the phone call to interrupt the radiologist. If the incoming matter 112 is a phone call about a non-urgent patient request, comms engine 102 will likely allow such phone call to be saved for later review. The decision making of the comms engine 102 shall be further described below and herein.

Figure 2:
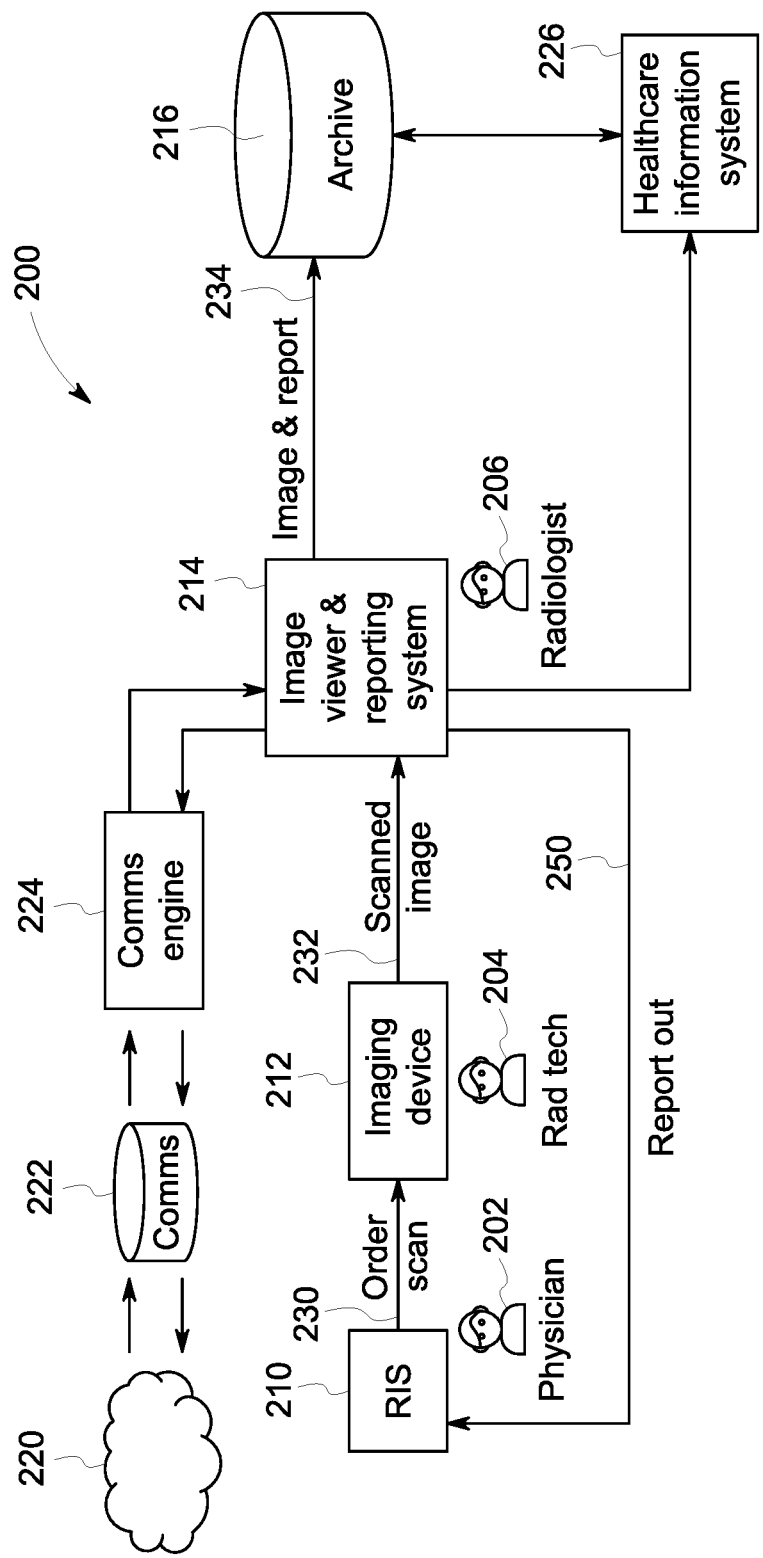
FIG. 2 shows a system in an interconnected radiology environment including a communication engine, according to an embodiment.

FIG. 2 shows a system 200 in an interconnected radiology environment including a communication engine, according to an embodiment. Physician 202 may be a referring or primary care physician who interacts with a patient to diagnose a medical issue. Through RIS (radiology information system) 210 they order an imaging scan 230 of a patient. Radiology tech 204 uses imaging device 212 to image the region of interest of a patient to produce scanned image 232. A radiologist uses image viewer and reporting system 214 to review scanned image 232 and provide a report 250 back to physician 202. Such images and reports 234 are also saved to archive 216 along with the related scanned image 232. Comms 222 as well as images and reports 234 can be further accessed by other uses of the healthcare information system 226. Comms engine 224 receives incoming comms 222 (also known as incoming matters) from network 220 and provides user generated as well as automatically generated response comms 222 back to network 220. Comms engine 224 interacts with image viewer and reporting system 214 to allow comms 222 to reach radiologist 206 at the most appropriate times to reduce unneeded interruptions and most efficient workflow. Network 220 may be any computer network system for communication, such as the internet, an intranet, and includes any wired or wireless computer communication systems.

Figure 3:
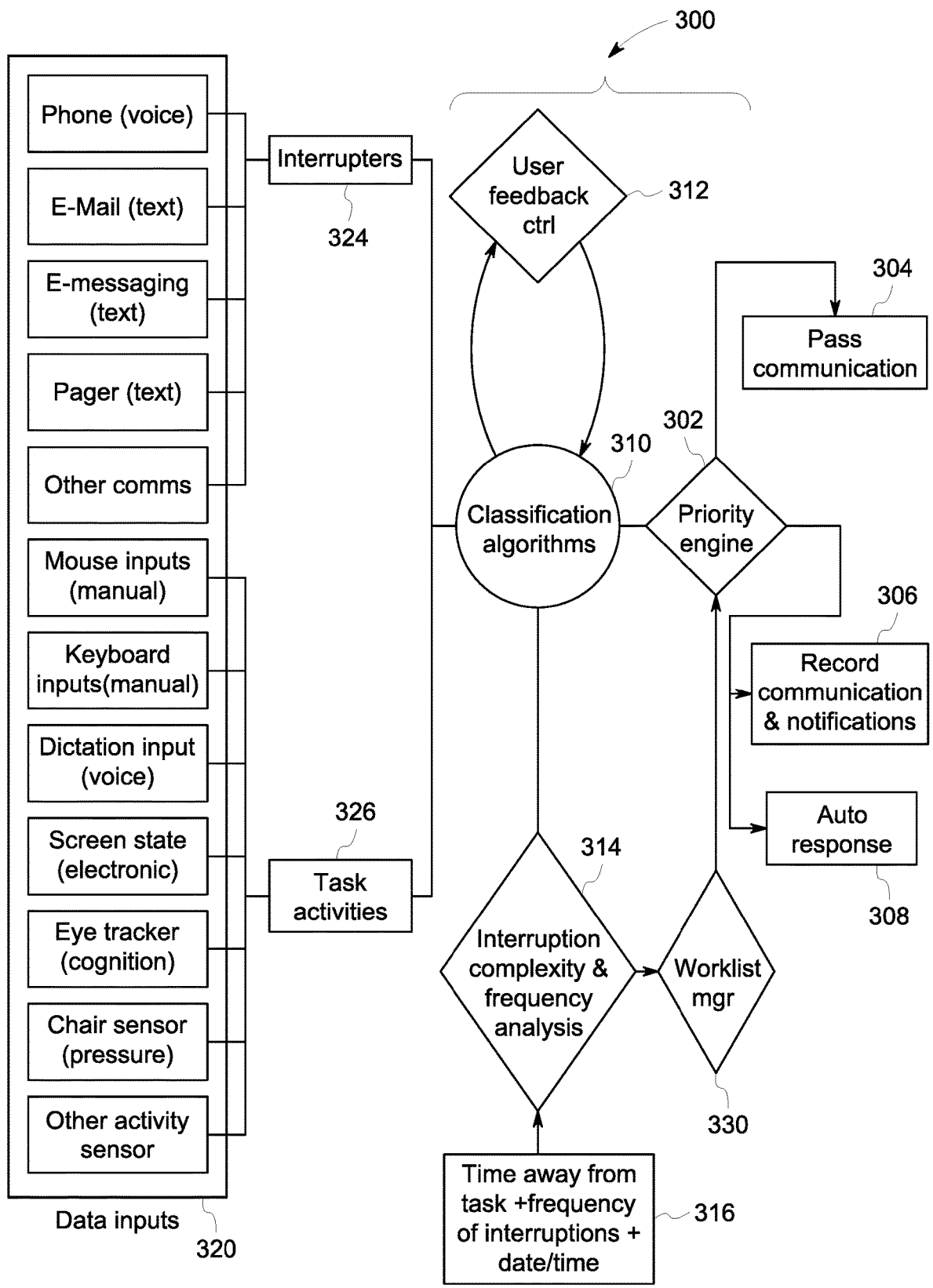
FIG. 3 shows process and system for improving input classification and interruption management, according to an embodiment.

FIG. 3 shows process and system for improving input classification and interruption management, according to an embodiment. FIG. 3 includes comms engine 300 which receives interrupters 324 and task activities 324 from various forms of data inputs 320 and provides output options, such as pass communication 304, record communication and notification 306 and auto response 308. Data inputs 320 may include incoming matters from physical people in the healthcare facility, phone calls, e-mails, e-messaging, text messages, pagers, and other forms of digital communication. Task activities 326 are the monitored state, context, and activities of a user in the healthcare technology system, with FIG. 1 and FIG. 2 as examples. Task activities 326 may be monitored by mouse input, keyboard inputs, voice input such as dictation, screen state of one or more computer devices a user may be using, eye tracking, chair sensors, hospital camera and microphones around the facility—either installed or on other computer or smart phone systems nearby, as well as other activity sensors. A further data input not shown is related to the hours, shift information, and time remaining at work for a user. Knowing the state of a user's workday can be vital for informed decisions regarding when best to display and provide certain communications.

FIG. 3 further includes classification algorithms 310, user feedback and control 312, interruption complexity and frequency analysis 314, time away from task plus frequency of interruptions plus date/time analysis 316, priority engine 302, worklist manager 330, pass communication 304, record communications and notifications 306, and auto response 308. Comms engine 300 may include, in certain embodiments, classification algorithms 310, interruption complexity and frequency analysis 314, time away from task plus frequency of interruptions plus date/time analysis 316, priority engine 302, and worklist manager 330.

Classification algorithms 310 are algorithms that classify the interrupters 324 and task activities 326 to understand what the incoming matter is and what state and activity the user is in currently. This includes cross-channel communication monitoring across the range of data inputs 320. Classification algorithms 310 may be rules engines, machine learning algorithms, deep learning algorithms, neural networks, and/or other forms of artificial intelligence algorithms. Classification algorithms may use keyword analysis. Classification algorithms may use user analysis not only of the user's task activity but also the user's level in the organization, title, and role.

Classification algorithms 310 leverage interruption complexity and frequency analysis 314 that evaluates the interrupters 324 as incoming matters try to rank whether it is standard message, urgent ("stat") message or other priority level. Interruption complexity and frequency analysis 314 helps to understand whether an incoming matter is a low priority and high frequency minor matter as well as higher priority low frequency matter. Matters may be any mix of priority level and frequency rate. Interruption complexity and frequency analysis receives input 314 leverages time away from task plus frequency of interruptions plus date/time analysis 316 in its analysis, which provides history information related to how the particular user may have handled previous interruptions. For example, if priority engine 302 passed a communication 304 to a user and it took that user 60 minutes to get back to focused work, but a second user got the same communication passed and got back to focused work in 15 minutes, the interruption complexity and frequency analysis 314 may keep passing future similar future communications to the second user but may record related communication and notification 306 for the first user moving forward. Interruption complexity and frequency analysis 314 further may provide information as to the specific user's ability or general responsiveness—providing information on how long it would take that specific user to respond.

Priority engine 302 receives the classification decisions and information from classification algorithms 310. With the classification decisions and information, priority engine 302 can prioritize the incoming matter 324 compared with the current task activity 326 and upcoming worklist from worklist manager 330. Since priority engine 302 is aware of the current worklist, priority engine can decide where best the interruption may fit in the overall flow of the future planned work for the day in comparison to how much time is left in the work shift. This allows for sophisticated and nuanced decisions about the interruption and the specific user. Another example is where there may be a lull in the activity or in the appointments for a physician, so priority engine 302 can record the communication and notification 306 for that future time when there is an expected lull.

Priority engine 302 as part of comms engine 300 makes decisions on what to output and how to handle the incoming matter or interrupter 324. One decision may be passing the communication 304 to the user right away, such as in high priority, urgent, or required situations (such as medically or legally required). Passed communication may include the original interrupter, but comms engine may append additional useful information about the interruption based on the classification algorithms. For example, a patient is requesting something urgent, and the passed communication not only includes the patient request but also the report from the latest patient visit from the EMR system. Another decision may be to record the communication and notification 306 for a future time, potentially later that day, during a lull, or other appropriate time. Such appropriate times may be specifically indicated by a user based on their own ability to edit the preferences and settings in the system through user feedback and control 312. Another decision may be to provide an automatic response 308. This is best in situations where specific information can be provided as already existing in medical data 114 or other data repository.

Further, priority engine 302 may also notice that the incoming matter may be best suited for a wholly different user and can pass the communication 304 to the other user. For example, when a nurse may be able to handle a request that came into a doctor. This saves the full interruption for the doctor, both currently and any future interruption.

User feedback and control is helpful for the improvement of the system. Comms engine 300 may include user interface prompts directly in passed communication 304 that ask for feedback, such as 'was this interruption the right time, if not when?' or 'would you have preferred this communication at the end of your shift'. Many other customized feedback queries may be generated. And similar feedback questions may be asked for later viewed interruptions by recorded communications and notifications 306. The user also may go into their own settings and edit how classification algorithms work, what priorities should be most important for priority engine, and other aspects related to their own work proficiency. This includes editable settings so that user can modify application performance to meet their expectations.

Figure 4:
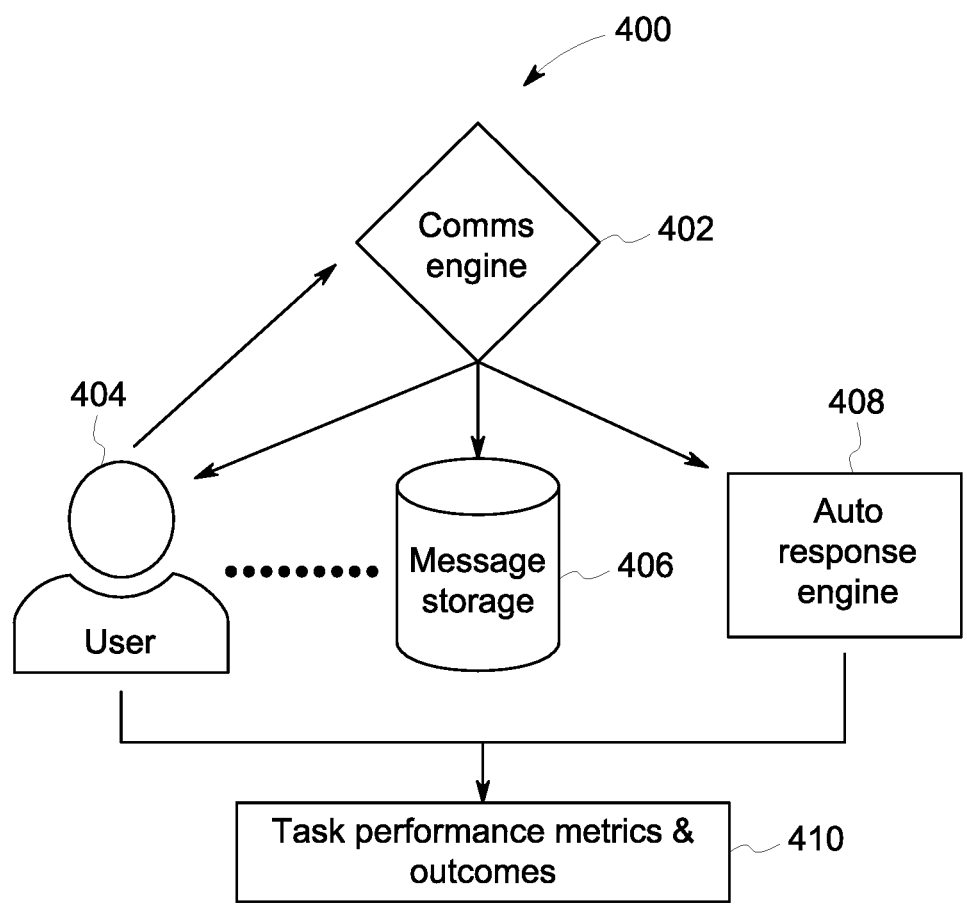
FIG. 4 shows a process and block diagram for improved communication management, according to an embodiment.

FIG. 4 shows a process and block diagram for improved communication management, according to an embodiment. FIG. 4 includes system 400, comms engine 402, user 404, message storage 406, auto response engine 408, and task performance metrics and outcomes 410.

Comms engine 402 receives incoming matters and makes decisions on when and how interruptions should affect user 410. Incoming matters may be messages, human interactions, files, reports, and other types of work actions that are asking for a user's response. A decision by comms engine 402 may be to pass the communication to user 404, sometimes with additional context and information. A decision by comms engine 402 may be to store the incoming matter for later in message storage 406. A decision by comms engine 402 may be to respond automatically to the originator of the incoming matter with auto response engine 408. After a decision is made, the system can evaluate based on the time taken, user feedback, and final outcome to determine the effectiveness of the comms engine decision in task performance metrics and outcomes 410.

Comms engine 402 may know from user patterns and/or user preferences which users may be able to handle more than one issue (individuals good at multi-tasking). Further, the decisions of comms engine 402 may change based on the day. For example, a user can generally set family messages to lower priority, but if there is an urgent issue or matter, the user can set for a time period that certain messages should always interrupt. As an example, a child is competing in a competition and user 404 want to hear right away how it ended, please pass through those messages right away instead of normally saving all messages from the child until the end of the day. The individual can set feedback on each message (having feedback options in the UI of the message displayed—such as 'see more like this' or 'always prioritize this message type') or go into a central settings and preferences menu to edit.

Monitoring the task state and messages of user 404 allows the system to support the user at the right time to avoid sub-optimal performance due to interruptions and the related switching. For example, if a user state is present or available messages can be sent to the user by comms engine 402, whether they are standard or urgent messages (urgent messages may also be stat messages, high priority messages, or life support decision messages). If the user is engaged, busy, or absent, comms engine 402 may send an automatic response from auto response engine 408 if the message is classifiable. If not classifiable (a type or subject not able to be determined by classification algorithms), comms engine 402 may just store the message in message storage 406. For urgent messages where an auto response can't or shouldn't be generated, the user can be interrupted with a plan for resumption assistance. For urgent messages where the user is absent, comms engine 402 can page the user.

Auto response engine 408 provides automatic responses related to the incoming matter. These automatic responses can be from a repository of standard responses, customized responses for individuals, or wholly new and specific responses based on machine learning or artificial intelligence tools.

Figure 5:
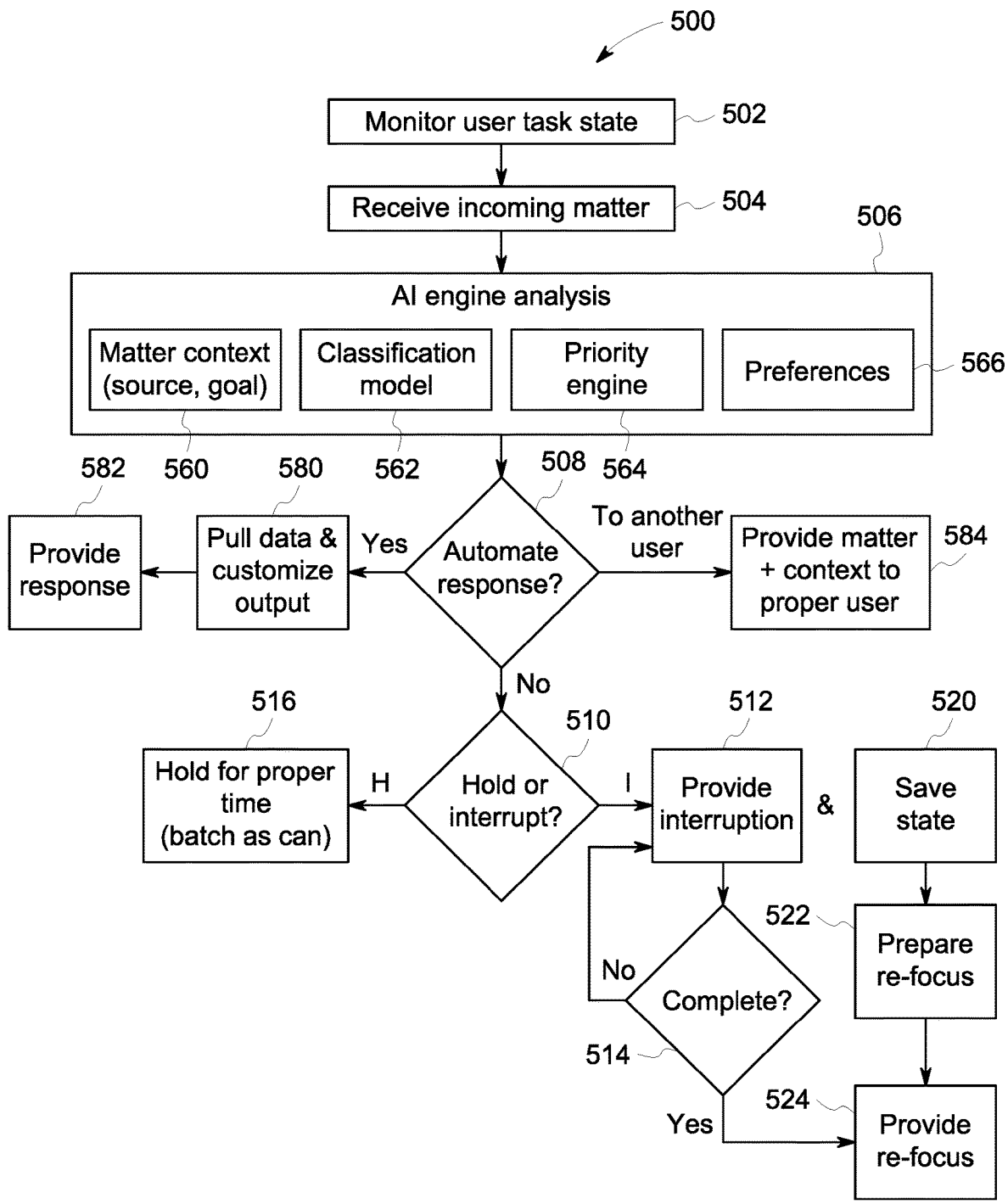
FIG. 5 shows a process for a communication engine to analyze inputs and make interruption and automation decisions, according to an embodiment.

FIG. 5 shows a process for a communication engine to analyze inputs and make interruption and automation decisions, according to an embodiment. FIG. 5 includes process 500 that may run within a comms engine, monitor user task state step 502, receive incoming matter step 504, AI engine analysis step 506, matter context 560, classification model 562, priority engine 564, preferences 566, automate response decision step, pull data and customize output step 580, provide response step 582, provide matter and context to proper user step 584, hold or interrupt decision step 510, hold for proper time step 516, provide interruption step 512, complete decision step 514, save state step 520, prepare re-focus step 522, and provide re-focus step 524.

Comms engine monitors the user state in step 502. As received incoming matters arrive at step 504, AI engine analysis occurs to understand the context of the incoming matter in step 560, classify the incoming matter in step 562, see the user preferences in 566, and finally decide a priority level of the incoming matter in step 564. If a response can be automated well based on the situation as determined in step 508, then comms engine pulls the data needed from hospital storage systems and customizes the output message to the originator of the incoming matter in step 580 and provides the response in step 582. This saves the time and focus of the intended recipient of the incoming matter. If another user is a better recipient for the incoming matter, the comms engine provides the matter and related context to the best user for the matter in step 584. If no automated action fits the situation, a hold or interrupt decision is made in step 510. This is primarily based on the output of the priority engine 564 combined with the other factors considered by the AI engine analysis step 506. If held, the communication is held for a proper time in step 516. Communications that may be batched, such as those related to the same patient or situation are put together for best processing. If the decision step 510 is to interrupt, the interruption is provided in step 512 and the system monitors how the user handles the situation and any other feedback in 514, which can be utilized in future analysis of step 506.

Preferences 566 may include individual preferences based on user activity, direct user settings, and user feedback. Preferences 566 may also include group level settings. This may be settings specific to the department in a hospital, the whole institution, or various subgroups. Group level settings may help to optimize a department as a whole. For example, if a department specifically designates time in radiologist schedules with no meetings so they can focus (such as at the end of the day when reports need to get submitted or earlier in the day if radiologists are more mentally efficient), there may be a higher priority set over that time compared with incoming matters. Preferences 566 may also have preferences based on best practices at other institutions, government laws or regulation, and/or medical associations.

Another feature of AI engine analysis is the ability to double check the incoming matter information. Sometimes the incoming matter may have incorrect information or assumptions, such as 'I came to your office last Thursday' when the patient truly came in a different day. Another example is an incoming matter simply asking for the wrong imaging study (give me the ultrasound images from September, when they meant the CT scans). The AI engine analysis step 506 can correct these issues before the user sees and this can prevent mistakes and potentially dangerous errors.

Process 500 helps to limit interruptions, automate communication tasks that don't require user interaction, (i.e., automatically respond to common questions such as, "Is my study ready?"), reduce context switching costs by only allowing external messages to be transmitted during lulls, and utilize artificial intelligence to identify when communication will have the lowest impact on other tasks.

Process 500 also has a ready to resume feature, further described hereinbelow related to additional figures. When an interruption occurs, the system saves the current state of the activity being performed in step 520 and prepares assistance for re-focusing in step 522. Once a user has completed the action, re-focus assistance is provided to help them resume where they left off in their previous activity. This can substantially save time and help prevent errors related to the human brain re-engaging with a previous activity. For example, if a physician is looking for medication for a patient and is interrupted for a priority question related to an ongoing surgery. The physician may forget what they were doing related to the medication or forget key details regarding the medication, allergies, dosage levels, etcetera. The ready to resume feature can provide this re-focusing context and information. The re-focus help may also pull up the exact computer screens the user was last at during the previous activity, and also can highlight on the screen exactly where they left off.

Some interruptions may be positive and help right now. For example, a radiologist is reviewing a radiology report and an interruption comes in from the patient stating the pain is in the right side of the brain. This would allow the radiologist to be able to give particular focus to that part of the anatomy during the current review they are doing, which may help the radiology report and medical diagnosis. Another example may be a doctor typing up a prescription and the system may interrupt and let him know a message from the nurse just came in related to patient allergies to the medication he is prescribing. AI engine analysis 506 would note the relevance of the received incoming matter 504 to the current user task state 502 and the interruption would be provided in step 512.

Figure 6A:
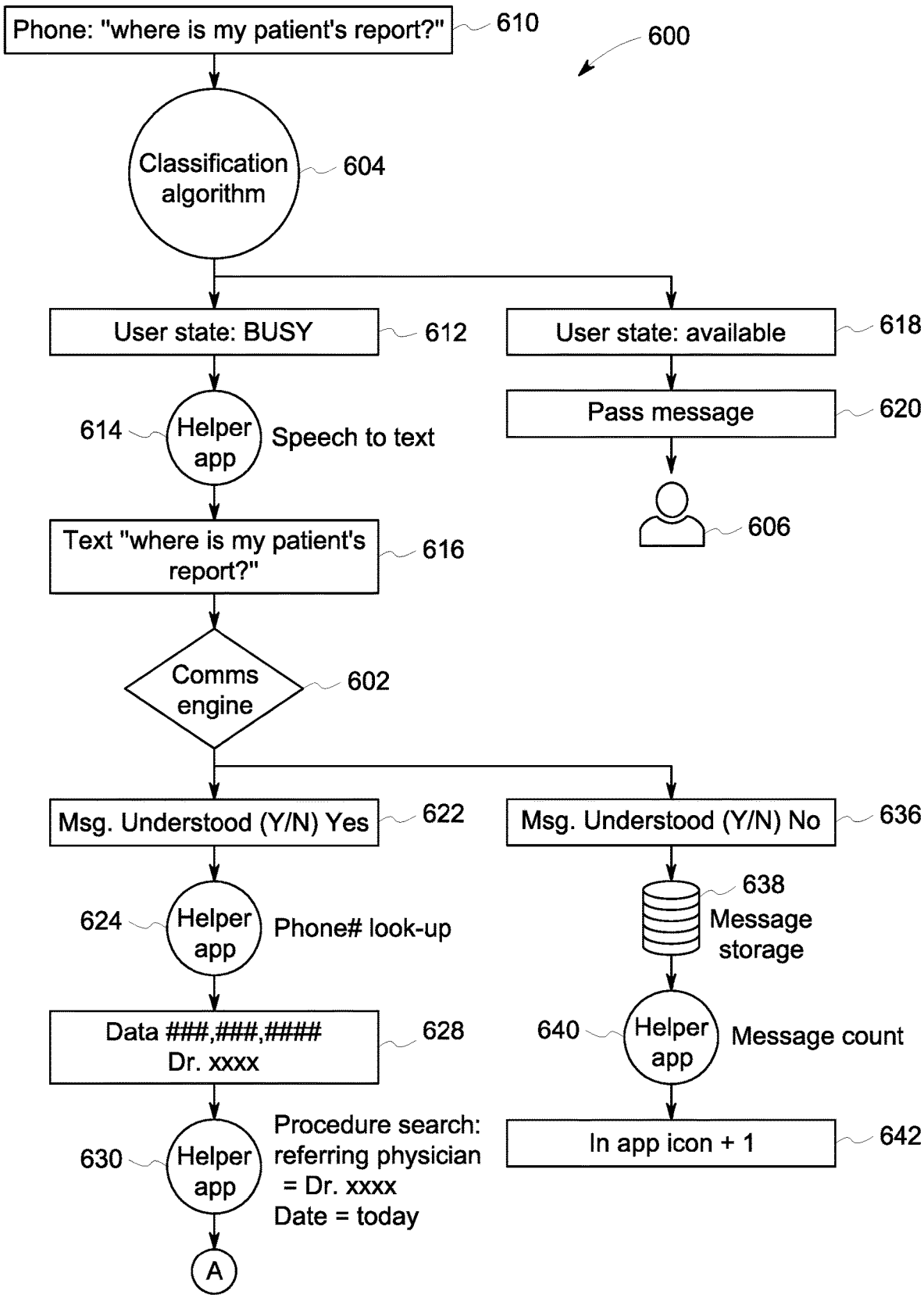
FIGS. 6A and 6B shows an exemplary process performed by a communication engine, according to an embodiment.
Figure 6B:
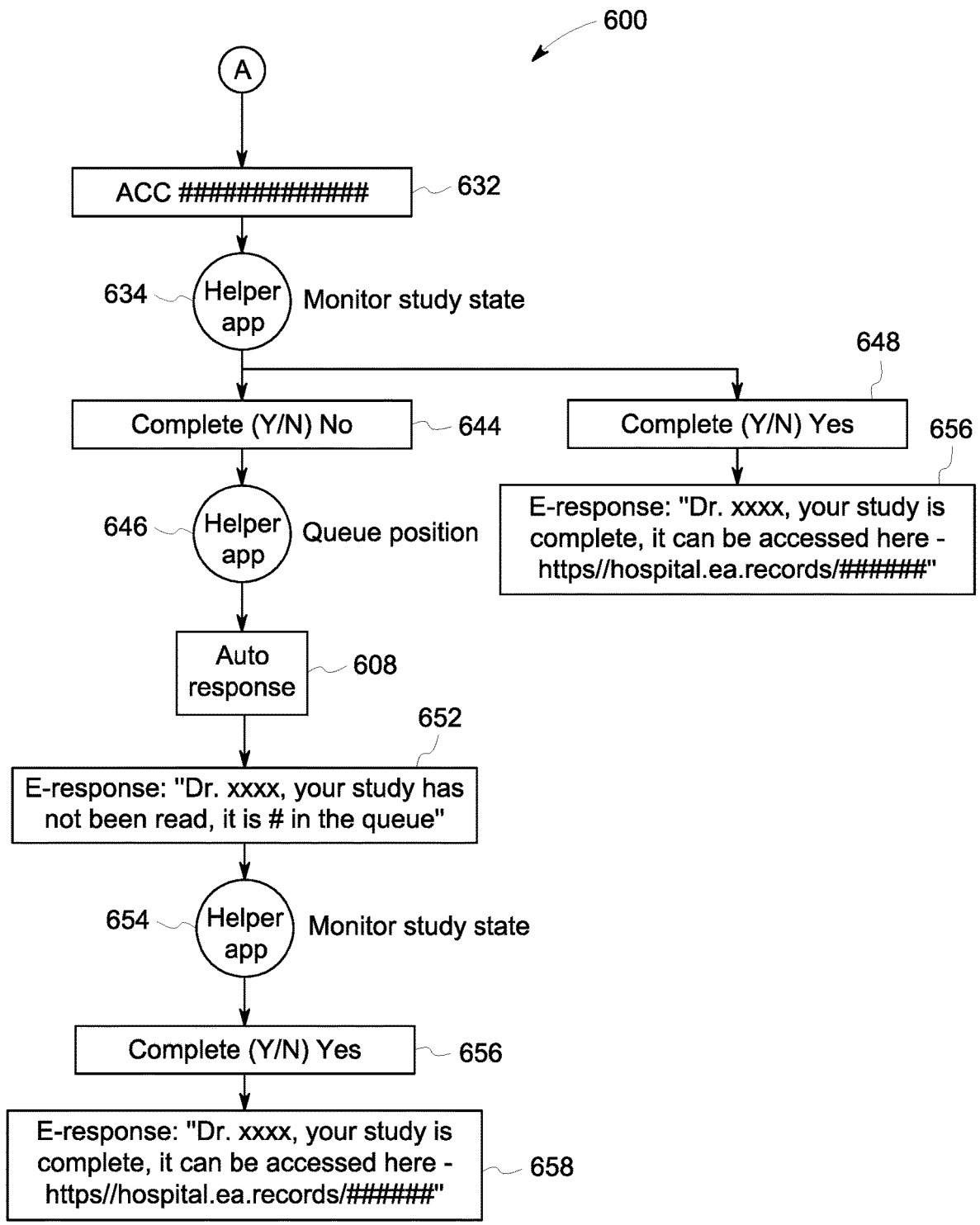

FIGS. 6A and 6B shows an exemplary process performed by a communication engine, according to an embodiment. Process 600 is only one example situation to help illustrate an embodiment, and is not meant to be limiting as to the functionality of the improved technology disclosed herein. Classification algorithm 604, process steps, and helper apps listed may be separate hardware or software modules in the system or may be within a comms engine.

In step 610, an incoming matter arrives into the computer technology system. In this example it is a phone call asking, "where is my patient's report?" This is likely from one medical professional to another.

In step 604, a classification algorithm analyzes the incoming matter. In this case it detects it is a phone message related to the work of recipient 606. Thus, the matter will go to recipient 606 and the question is when and how a response should be generated, either automatically, by the recipient, or by another user.

In step 618, the user state is detected as available, the process moves to step 620. This indicates the user would not be significantly interrupted by an incoming matter currently. It is likely a good time to provide matters for review.

In step 620, the message from step 610 is passed to recipient 606. Step 620 can also pass the message with additional user interface (UI) buttons appended to the original message. This allows recipient 606 to provide feedback to the system for improving in the future (such as 'Was this ok to pass through?', 'Is there an automated response you want next time?').

In step 612, the user state is detected as busy. This may mean that the recipient 606 is currently engaged in a task and the incoming matter does not have a higher priority than the current task activity. Such a priority determination may be made by a priority engine. For example, if the recipient 606 is a surgeon actively in surgery, a query about a patient report should be held until after the surgery is over.

In step 614, a helper app (a hardware or software module either separate from or within a comms engine) performs a speech to text rendering of the phone message. In some embodiments, a text to speech rendering may occur, including in situations where the recipient is using a voice assistant and hearing their incoming matters as opposed to seeing them on a computer screen.

In step 616, the text "where is my patient's report?" is passed to comms engine 602. Process 600 then performs steps to determine how best to handle the incoming matter based on the current situation, incoming matter type and priority, and preferences of the user.

In step 636, the comms engine 602 was unable to understand the message (Msg. Understood No). In this instance, the message is stored in message storage 638. If related to other incoming matters, they may be batched together. In step 640, a helper app adds to the recipient's message count and their communication system is updated in step 642 to show an additional new message, such as their app icon showing a +1. This allows the recipient to be aware of the new incoming matter and handle it when they have some free time to do so.

In step 622, comms engine 602 was able to understand the message (Msg. Understood Yes). Since the process understands the message, it can evaluate whether it can be automatically helpful to the recipient. This may save time, frustration, and money.

In step 624, a helper app looks up the phone number related to the phone message. This allows the system to determine more information about the incoming matter.

In step 628, the phone number data and related physician requesting the information is retrieved.

In step 630, a helper app does a procedure search based on the referring physician with the date of today. The helper app is determining if it can automatically find the patient report that is the subject of the phone request. In this example the helper app is able to find the report, but in cases where it cannot, it may send a text message back to the physician asking more information about which patient and what type of report. This automatic information gathering can be helpful to provide automatic support and/or for the recipient 606 if they review the request.

In step 632, the patient report is identified (ACC ##########) by the system based on the incoming matter information and additional information determined by the system in steps 628 and 630.

In step 634, a helper app monitors the study state. If the study state is complete, the process moves to step 648. If the study state is incomplete, the process moves to step 644.

In step 648, the study is complete, so the report is ready for the referring physician.

In step 656, the process (likely through a comms engine) provides an automatic response. In this example it says "Dr. xxxx, your study is complete, it can be accessed here—https//hospital.ea.records/######." In this instance the recipient 606 never was interrupted and the individual who submitted the incoming matter is helped promptly.

In step 644, the study is incomplete, and the process moves to step 646.

In step 646, a helper app works to be helpful by looking up the queue position of the report. This is related to the worklist for the recipient 606, trying to determine how soon they will review the study and generate the report for the requester. If it cannot automatically provide the report requested, it tries to give a status update to the referring physician.

In step 608, an automatic response is generated for the requester giving them a status update on their request.

In step 652, the response is provided electronically. In this case it says "Dr. xxxx, your study has not been read, it is # in the queue." This is at least prompt response with an update that does not interrupt recipient 606.

In step 654, a helper app monitors the study state. When the study is complete and the report is ready, the process moves to step 656.

In step 656, the report is ready for the requester and is provided in step 658. In this case it says "Dr. xxxx, your study is complete, it can be accessed here—https//hospital.ea.records/######." Throughout the whole of process 600, recipient 606 is allowed to focus and work most productively. No interruption of their work occurs which may happen when a normal phone call arrives in other environments.

Figure 7:
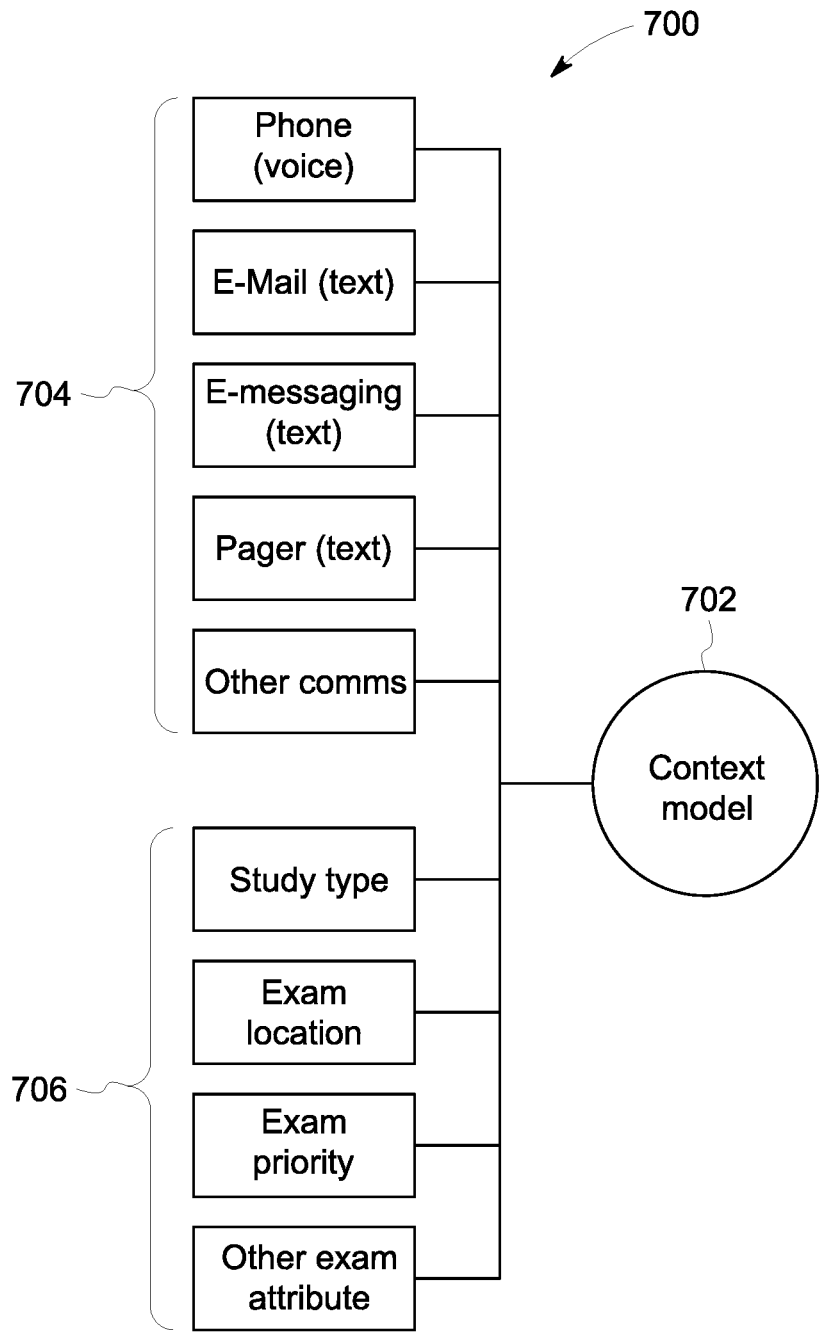
FIG. 7 shows a block diagram for context model development, according to an embodiment.

FIG. 7 shows a block diagram for context model development, according to an embodiment. System 700 includes context model 702, inputs 704, and attributes 706. Inputs 704 may be phone (voice), e-mail (text), e-messaging (text), pager (text), and/or other communication methods. Attributes 706 may be study type, exam location, exam priority, and other attributes of an exam. In this example, exams are imaging scans or other medical examinations.

The goal of system 700 is to understand the context in the healthcare system, especially studying the user who may be interrupted in the future. Context model 702 uses inputs 704 and attributes 706 to build a model of the regular incoming matters a user may receive and also the general worklist for the user. The final context is an understanding as to where the incoming matter from inputs 704 may compare to the work attributes 706. All of this feeds into an understanding of when interruptions and which interruptions may best fit for the particular user. System 700 determines when an interruption will have the least impact based on the lulls in activity and minimization of return to task time. Lulls in user activity are an opportunity for message notification or transmission. Context model 702 will specify BUSY initiation criteria and AVAILABLE criteria. The goal is to identify which communications are time sensitive and which can be deferred based on user feedback to system (e.g., which communications are ignored, which immediately responded to, etc.). Context model 702 also can build an allow list and block list of communication channels. It will also ascribe a weighting function for study attributes based on the speed with which the user responds to the communications. These lists and weights are editable by a user, and an emergency override is available as well to override context model 702 when needed.

Context model 702 may be a rules engine model, machine learning model, neural network model, deep learning model, and/or artificial intelligence model. System 700 continues to adjust criteria (continuous training mode) as user engages with system. And the criteria for busy and available, as well as other user specific understandings can be editable by the user, creating a flexible system with a lot of precise control while still allowing the comms engine to automatically do the work most of the time. System 700 may be included within a comms engine.

Figure 8:
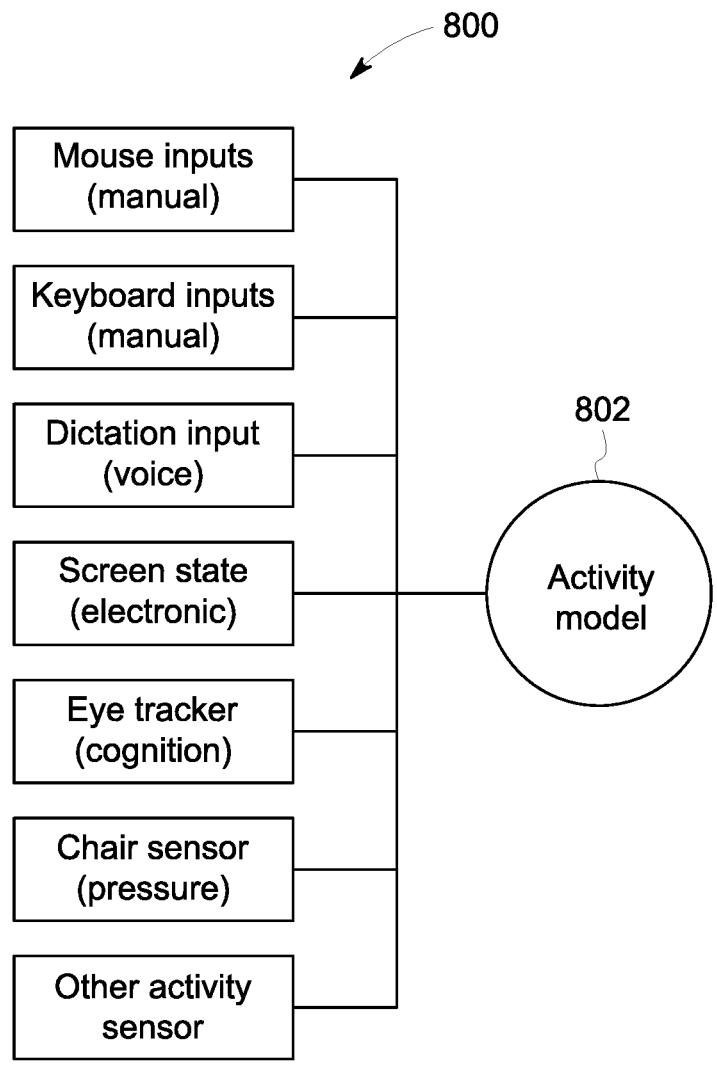
FIG. 8 shows a block diagram for activity model development, according to an embodiment.

FIG. 8 shows a block diagram for activity model development, according to an embodiment. System 800 includes inputs and sensors that feed into activity model 802. Activity model uses mouse inputs, keyboard inputs, dictation input, screen state, eye tracking, chair sensor, and other inputs and sensors to build a model of the user's patterns of activity to identify which inputs co-occur, and to help determine when the user is most productive. All of this feeds into an understanding, along with the context model, of when interruptions and which interruptions may best fit for the particular user. Activity model 802 may be a rules engine model, machine learning model, neural network model, deep learning model, and/or artificial intelligence model. System 800 continues to adjust criteria (continuous training mode) as user engages with system. System 800 may be included within a comms engine.

Figure 9:
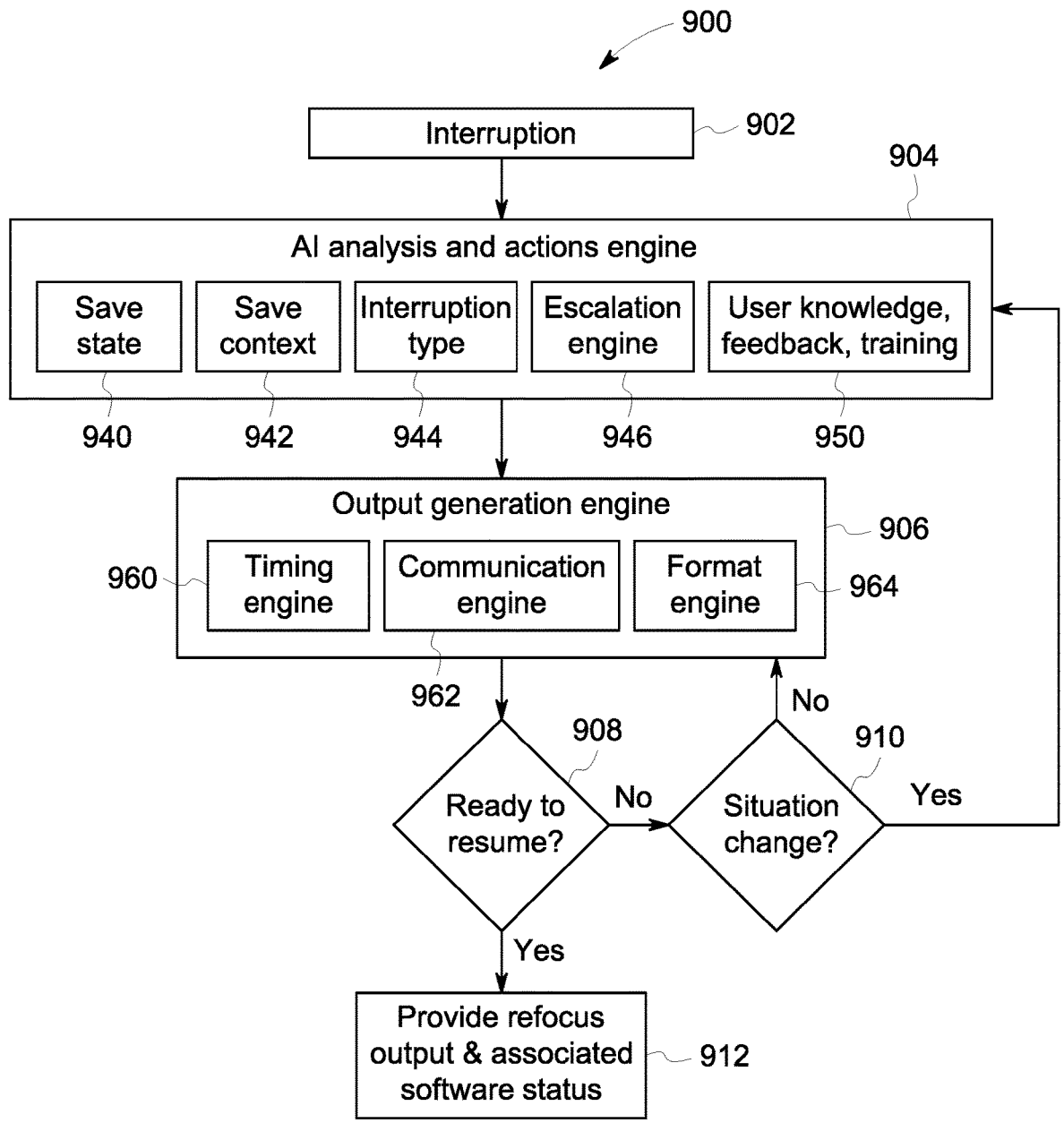
FIG. 9 shows a process and system for assisting a user on resuming activity after an interruption, according to an embodiment.

FIG. 9 shows a process and system for assisting a user on resuming activity after an interruption, according to an embodiment. This may be referred to as re-focus or ready-to-resume support. When users are interrupted and then return to their previous task, it is easy (and natural) for an individual not to remember which part of the last task was last completed. The amount of memory loss of the previous task depends on the characteristics of the previous task itself and of the interruption. Ready-to-resume support helps users take less time to re-focus on their previous activity, yet it yields significant benefits. This simple and brief practice of the technology systems and methods taking stock of where one stands on an interrupted task and briefly planning one's return helps the brain feel more at ease with putting it aside and switching attention to an interrupting demand.

System 900 includes interruption step 902, AI analysis and actions engine 904, output generation engine 906, ready to resume decision 908, situation change decision 910, and provide refocus output and associated software status step 912. As interruptions 902 are approved by the comms engine for the user, a ready to resume process takes place.

AI analysis and actions engine 904 saves state 940 of the user's current task which allows the system to revert the technology system back to that state when a user is ready to resume. For example, if a certain imaging exam was on the screen and the associated radiology report was being edited and on page 3, this context can be saved and be ready to be presented again in step 912.

AI analysis and actions engine 904 saves the context 942. The saved context are other factors related to where the user was at in the task and thinking, may be what the environment in the room is, the last few buttons or UI items the user clicked on last, or the last few words the user spoke out loud before being interrupted. Such additional context may be useful to trigger the user's brain to exactly where it left off in the train of thought.

AI analysis and actions engine 904 uses the interruption type 944 to understand how much time the current interruption may take. If the interruption may take the rest of the users work shift on a day, then the ready to resume feature may provide a different output compared to a five minute interruption. Further if the interruption type is personal in nature, then the computer system may not need to switch screens/user interface as compared to a medical related issue where the user may use their computer system to look at the information related to the new interruption.

AI analysis and actions engine 904 includes an escalation engine 946 that monitors the task left off and if the situation changes it can escalate the previous task again for the user. For example, if a patient needs the report, information, or medication that was being worked on, and the user has spent too much time on the interruption, this can factor in as to when, how, and with what output the ready to resume output is provided.

AI analysis and actions engine 904 includes user knowledge, feedback, and training 950. This allows the user to provide feedback and interact at how best they like to be assisted upon resuming tasks. The AI can learn from machine learning, deep learning, and other artificial intelligence methods of learning user responses.

Output generation engine 906 prepares the final refocus output and provides the associated software status that should be displayed upon the ready to resume step 912. Output generation engine 906 includes timing engine 960 which helps set the right timing for ready to resume outputs, in consideration of the user worklist, time of day, work shift information, and meeting schedule. Further, users may be more willing to resume a task at certain times of the day, such as after being refreshed with exercise, food, or fresh air. Output generation engine 906 includes communication engine 962 which provides the actual text of a communication to the user. For example, "You were most recently working on ultrasound radiology report for patient Betty Smith, click here to have the related report and ultrasound exam displayed on the screen." Output generation engine 906 includes format engine 964 that formats the output communication. If the user is now at a different environment and digital device than when they were last working on the previous task, formatting may be different. Format may be in audio form through a virtual digital assistant, through the user smartphone, and/or on the desktop computer. In addition, format engine 964 may append and provide feedback options related to the ready-to-resume feature, to collection learning for user knowledge, feedback, and training 950. After output generation engine 906 is completed, a ready-to-resume output message and associated software status is ready for the user.

At ready to resume decision 908 the system detects whether a user has completed interaction with interruption 902 and is ready to resume their previous activity. If so, the system provides refocus output and associated software status 912. If the user is not ready, the system monitors the current situation at step 910 to determine whether to re-adjust the output or AI analysis. Such a system saves time and money for healthcare operators, and is more helpful and enjoyable to the users.

Figure 10:
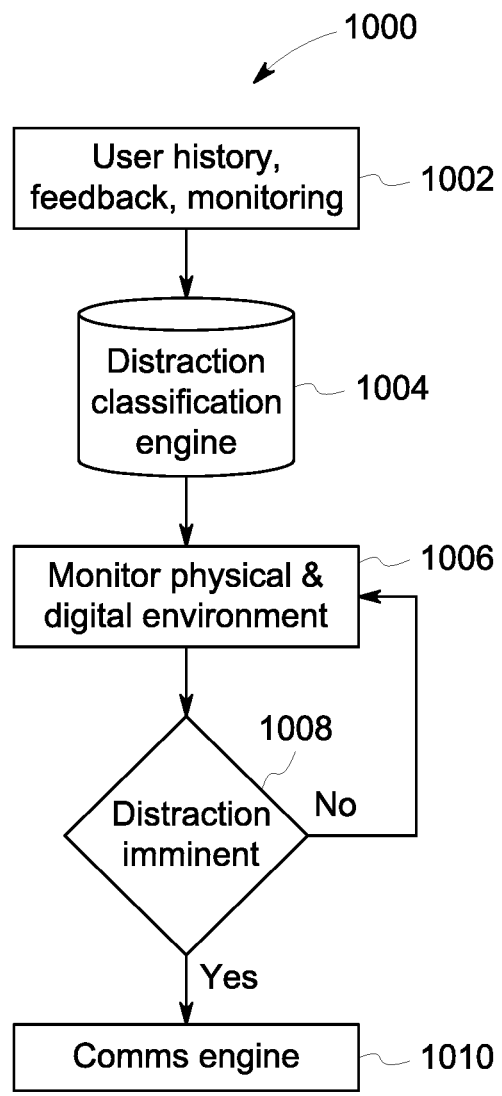
FIG. 10 shows a process and system for distraction detection and decision making, according to an embodiment.

FIG. 10 shows a process and system 1000 for distraction detection and decision making, according to an embodiment. The history of a user, feedback from the user, and monitoring of the current situation and activities of the user are tracked in step 1002. This provides an understanding of the current availability and busyness of the user. Further, certain things may distract some users and may not distract others, which is why history tracking for specific users is good. Some people look up from their desk every time people walk by, while others can remain focused on their task activity.

Distraction classification engine 1004 monitors the physical and digital environment for potential distractions to a focused user in step 1006. Physical distractions may be humans coming toward the user to talk to them. Physical distractions may be detected by cameras and microphones in computer devices around the work location, such as security cameras, desktop computers, and smart phones. Digital distractions may be smartphone games, other workers in a chat window, e-mails, etcetera. If distraction classification engine detects an imminent distraction 1008, it may feed this as a potential interruption or incoming matter to comms engine in step 1010. Thus, a distraction may feed into the interruption handling and ready-to-resume features described herein.

Figure 11:
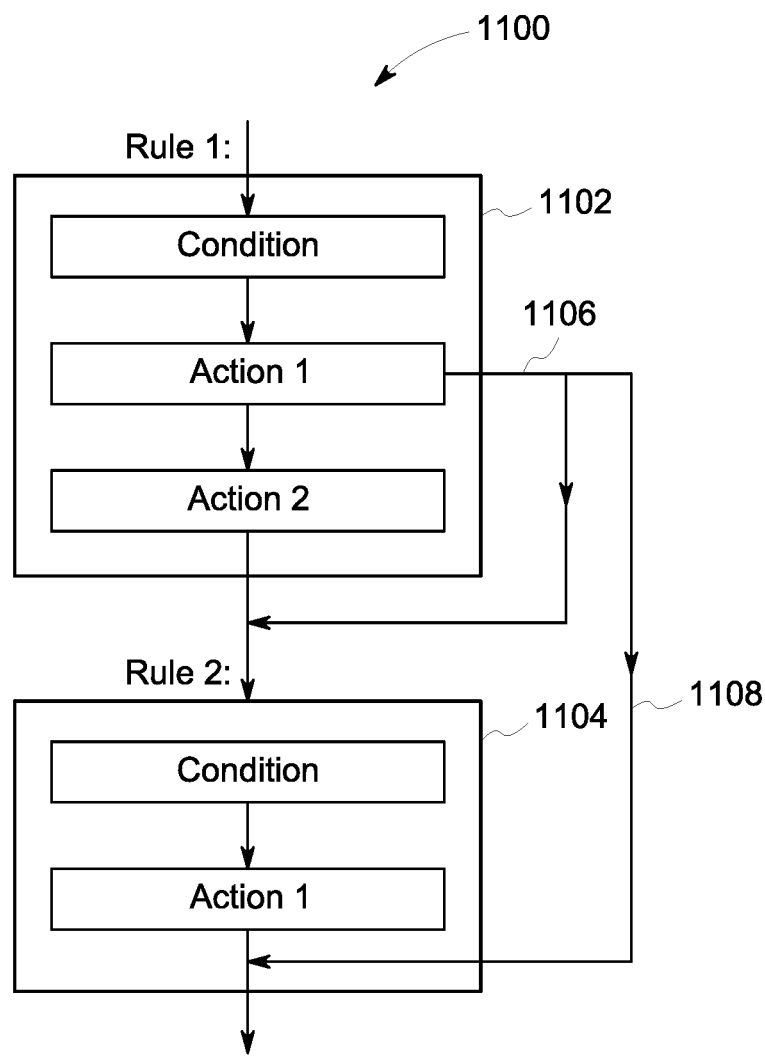
FIG. 11 shows another process and block diagram for rules in a rule engine, according to an embodiment.

FIG. 11 shows another process and block diagram for rules in a rule engine, according to an embodiment. Such a rule engine may apply to determine which user is the right one for a task, or as part of a context model or activity model. FIG. 11 includes rule engine process 1100, rule one 1102, rule two 1104, skip actions step 1106, and skip rules step 1108. FIG. 11 shows a situation where there is an error or other issue when executing an action based on a rule match. This may arise when the action is attempted at the wrong time, cannot execute based on report status, or other issues based on the specific rule engine. In this instance, the actions for the rule may be skipped in step 1106. Or, if the rule engine itself is no longer applicable based on the type of error or issue, the remaining rules of the ruleset or the whole rule engine may be skipped in step 1108.

Figure 12:
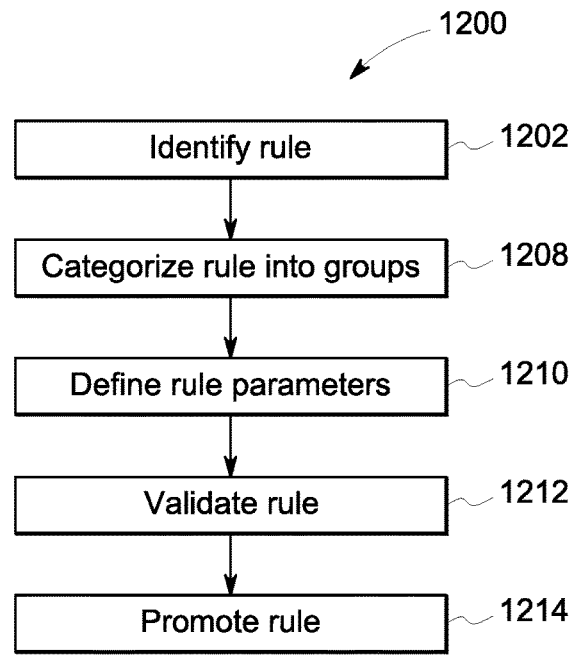
FIG. 12 shows a process for rule authoring, according to an embodiment.

FIG. 12 shows a process for rule authoring, according to an embodiment. Rule authoring helps users edit and provide feedback to the comms engine. FIG. 12 includes rule authorizing process 1200, identify rule step 1202, categorize rules into groups step 1208, define rule parameters step 1210, validate rule step 1212, and promote rule step 1214. Rule authoring may be completed by an authorized person with clinical knowledge to understand rule evaluation outcomes on patient safety. Such an authorized user may create new rules and edit existing rules. In step 1202, the systems and methods herein receive the rule from the user and create a new rule record, identifying the rule for the system. In step 1208, the systems and methods herein categorize the rule into the proper rule engine (if not pre-selected by the user) and into the associated rule groups. In step 1210, the systems and methods herein receive parameters from the user, and adds them to the rule information, such as the triggers and conditions for applying the rule and the actions that the rule takes based on various triggers and conditions. This includes, for example, sequence or order of applying the rule or if the rule is overridable or not. In step 1212, the systems and methods herein validate the rule, running a validation process to make sure the rule will execute successfully in the associated rule engine. If not, a prompt may issue to the user for updating the rule accordingly. In step 1214, the systems and methods herein promote the rule into the rule engine as a rule to be used in production as part of the associated rule engine. In addition, sometimes rules may be generated in a centralized manner across the industry and promoted to the rule engines all over the industry systems. For example, an employee for the government may generate a new rule related to legal requirements or financial requirements and promote that rule to the associated rule engines of the healthcare systems running those engines. This may apply if certain interruptions are required to be handled first or with priority.

Figure 13:
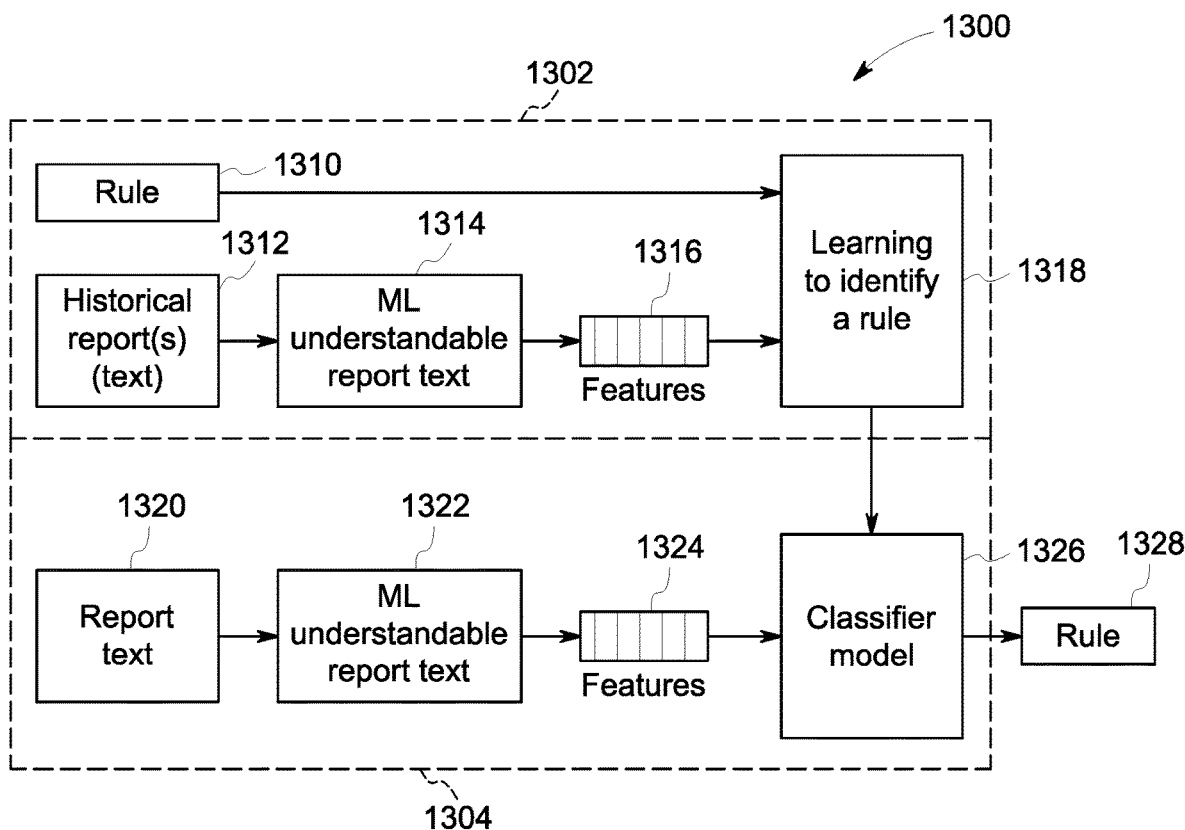
FIG. 13 shows a learning engine, according to an embodiment.

FIG. 13 shows a learning engine, according to an embodiment. Such a learning engine may be employed for classification models, activity models, context models, and the other AI analysis and engines described herein. FIG. 13 includes learning engine 1300, training engine 1302, prediction engine 1304, rule 1310, historical report text 1312, machine learning ("ML") understandable report text 1314, features 1316, learning to identify a rule 1318, report text 1320, ML understandable report text 1322, features 1324, classifier model 1326, and rule 1328. Artificial intelligence, deep learning, machine learning, and recumbent learning may be applied as part of rule engines, and FIG. 13 is just one example of a learning engine.

In training engine 1302, historical reports, interruptions, and user activity 1312 is mined and converted into ML understandable text 1314. The ML understandable text is run through machine learning algorithms (or other artificial intelligence, deep learning, or recumbent learning algorithms) to extract features 1316 related to the activity, interruption, or context depending on the situation. Then learning to identify a rule step 1318 takes rule 1310 and the extracted features 1316 and updates a classifier model 1326 based on the related learnings. In prediction engine 1304, the current report text 1320 is converted into ML understandable report text 1322. Current report text may be the new interruption, activity, or context in differing scenarios. The ML understandable text is run through machine learning algorithms (or other artificial intelligence, deep learning, or recumbent learning algorithms) to extract features 1324. Classifier model 1326 takes the output of training engine 1302 and the current report features 1324 to apply and improve rules 1328. Rule 1328 is then fed back into 1310 to continue to be improved through the learning engine 1300. Thus, learning engine 1300 receives reports and activity and uses machine learning to extract features to provide update actions models for classification, context, and activity, in an embodiment.

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

Figure 14:
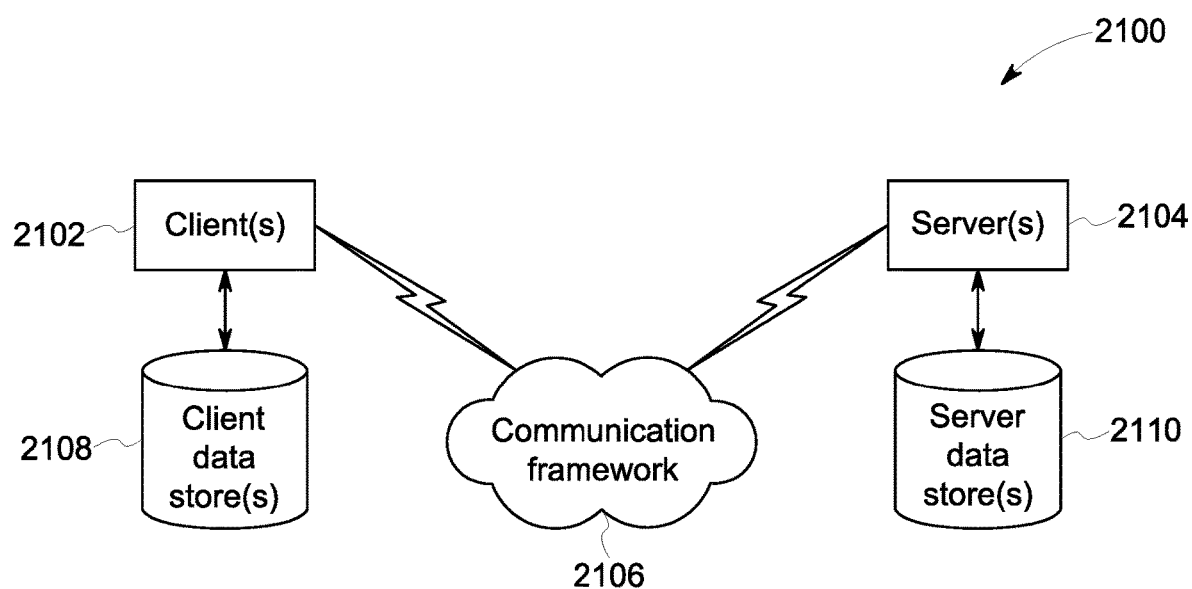
FIG. 14 shows a schematic block diagram of a sample-computing environment, according to an embodiment.

Referring to FIG. 14, there is illustrated a schematic block diagram of a computing environment 2100 in accordance with this disclosure in which the subject systems, methods and computer readable media can be deployed. The computing environment 2100 includes one or more client(s) 2102 (e.g., laptops, smart phones, PDAs, media players, computers, portable electronic devices, tablets, and the like). The client(s) 2102 can be hardware and/or software (e.g., threads, processes, computing devices). The computing environment 2100 also includes one or more server(s) 2104. The server(s) 2104 can also be hardware or hardware in combination with software (e.g., threads, processes, computing devices). The servers 2104 can house threads to perform transformations by employing aspects of this disclosure, for example. In various embodiments, one or more of the subject front end-components can be deployed as hardware and/or software at a client 2102 and one or more of the subject back-end components can be deployed as hardware and/or software at server 2104. One possible communication between a client 2102 and a server 2104 can be in the form of a data packet transmitted between two or more computer processes wherein the data packet may include video data. The data packet can include a metadata, e.g., associated contextual information, for example. The computing environment 2100 includes a communication framework 2106 (e.g., a global communication network such as the Internet, or mobile network(s)) that can be employed to facilitate communications between the client(s) 2102 and the server(s) 2104.

Communications can be facilitated via a wired (including optical fiber) and/or wireless technology. The client(s) 2102 include or are operatively connected to one or more client data store(s) 2108 that can be employed to store information local to the client(s) 2102 (e.g., associated contextual information). Similarly, the server(s) 2104 are operatively include or are operatively connected to one or more server data store(s) 2110 that can be employed to store information local to the servers 2104.

In one embodiment, a client 2102 can transfer an encoded file, in accordance with the disclosed subject matter, to server 2104. Server 2104 can store the file, decode the file, or transmit the file to another client 2102. It is to be appreciated, that a client 2102 can also transfer uncompressed file to a server 2104 and server 2104 can compress the file in accordance with the disclosed subject matter. Likewise, server 2104 can encode video information and transmit the information via communication framework 2106 to one or more clients 2102.

Figure 15:
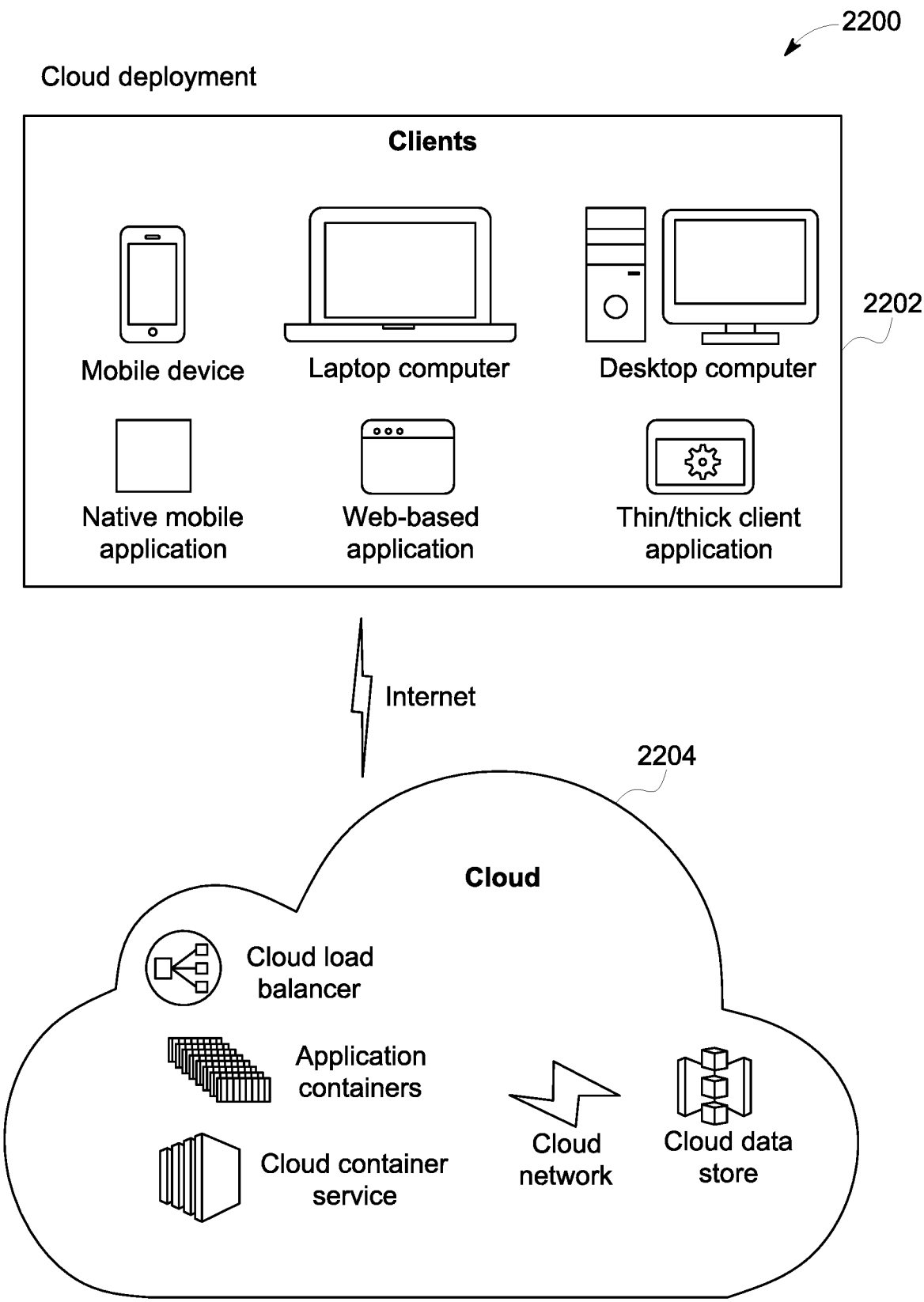
FIG. 15 shows a schematic block diagram of another sample-computing environment, according to an embodiment.

FIG. 15 illustrates a schematic block diagram of another example computing environment 2200 in accordance with this disclosure in which the subject systems, methods and computer readable media can be deployed. The computing environment 2200 includes a cloud deployment architecture consisting of one or more clients 2202 that can be communicatively coupled to a system cloud 2204 via a network (e.g., the Internet). The system cloud 2204 can include a cloud load balances, one or more application container, one or more cloud service containers, a cloud data store, and a cloud network that communicatively couples the one or more cloud components to the cloud data store. In accordance with the cloud deployment architecture, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems deployed in the system cloud 2204. In various implementations, the one or more components of system 100 can be distributed between the clients 2202 and the system cloud 2204.

Figure 16:
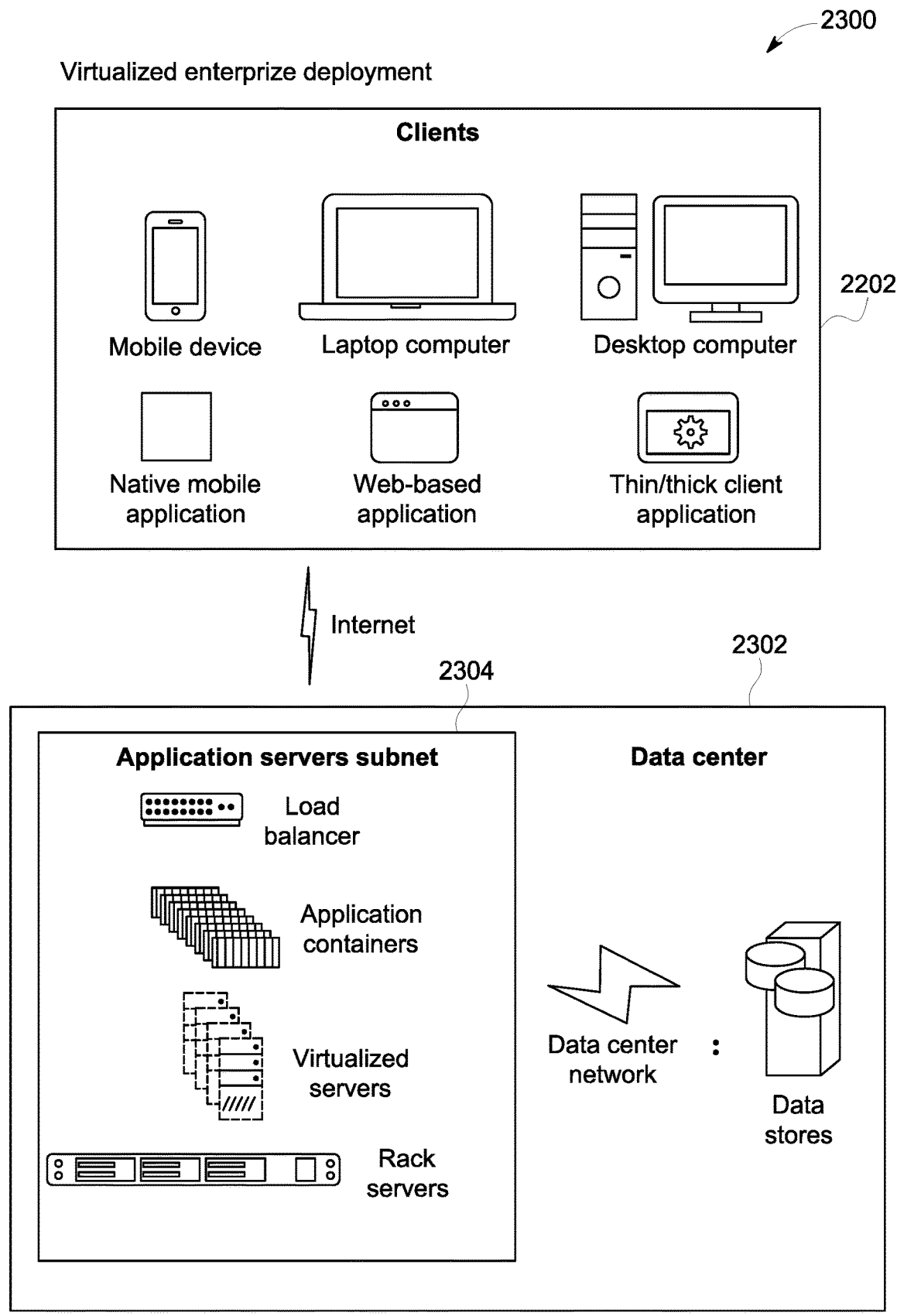
FIG. 16 shows a schematic block diagram of another sample-computing environment, according to an embodiment.

FIG. 16 illustrates a schematic block diagram of another example computing environment 2300 in accordance with this disclosure in which the subject systems, methods and computer readable media can be deployed. The computing environment 2300 includes a virtualized enterprise deployment consisting of one or more clients 2202 that can be communicatively coupled to a remote data center 2302 via a network (e.g., the Internet). The remote data center 2302 can include an application servers subnet 2304 which can provide a load balancer, one or more application containers, one or more virtualized servers and one or more rack servers. The data center 2302 can also include one or more data stores that can be communicatively coupled to the application servers subnet 2304 via a data center network. In accordance with the virtualized enterprise deployment, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems deployed in the data center 2302 and application servers subnet 2304. In various implementations, the one or more components of systems 100 can be distributed between the clients 2202 and the application servers subnet 2304 and the one or more data stores can be provided remotely at the data center 2302.

Figure 17:
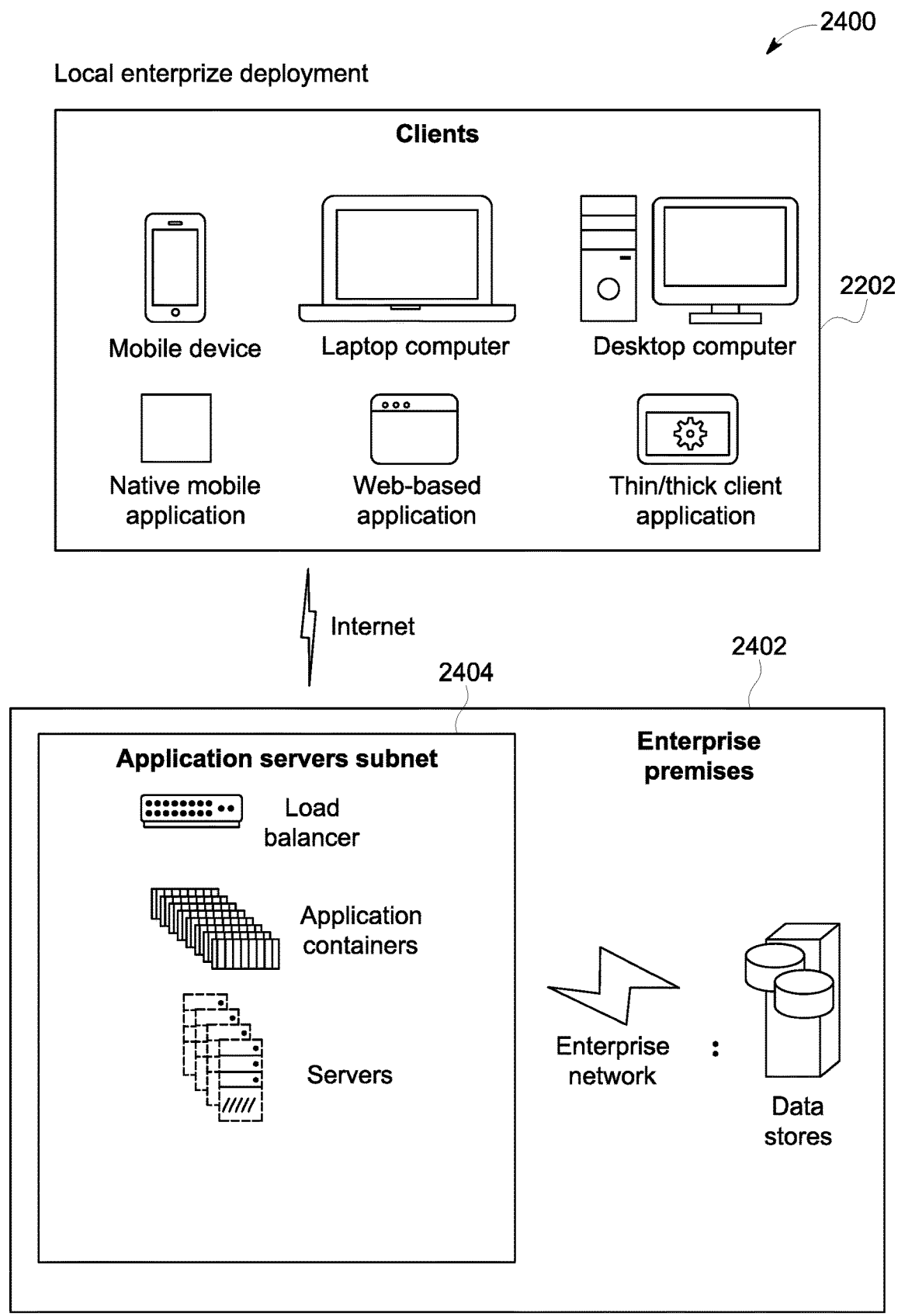
FIG. 17 shows a schematic block diagram of another sample-computing environment, according to an embodiment.

FIG. 17 illustrates a schematic block diagram of another example computing environment 2400 in accordance with this disclosure in which the subject systems, methods and computer readable media can be deployed. The computing environment 2400 includes a local enterprise deployment consisting of one or more clients 2202 that can be communicatively coupled to an application servers subnet 2404 via a network (e.g., the Internet). In accordance with this embodiment, the application servers subnet 2404 can be provided at the enterprise premises 2402 (e.g., as opposed to a remote data center 2302). The application servers subnet 2404 can include a load balancer, one or more application containers and one or more servers. The application servers subnet 2404 can be communicatively coupled to one or more data stores provided at the enterprise premises 2402 via an enterprise network. Similar to the cloud and virtualized enterprise deployments, the clients 2202 can include one or more clients devices (e.g., a mobile device, a laptop computer, a desktop computer, etc.) which can include or employ a suitable application (e.g., a native mobile application, a web-based application, a thin/thick client application, etc.) to access and employ one or more features and functionalities of the subject native/reconstructed medical imaging systems (e.g., system 100 and the like) deployed at the enterprise premises 2402 and the application servers subnet 2404. In various implementations, the one or more components of systems herein can be distributed between the clients 2202 and the application servers subnet 2404 and the one or more data stores can be provided at the enterprise premises 2402.

Figure 18:
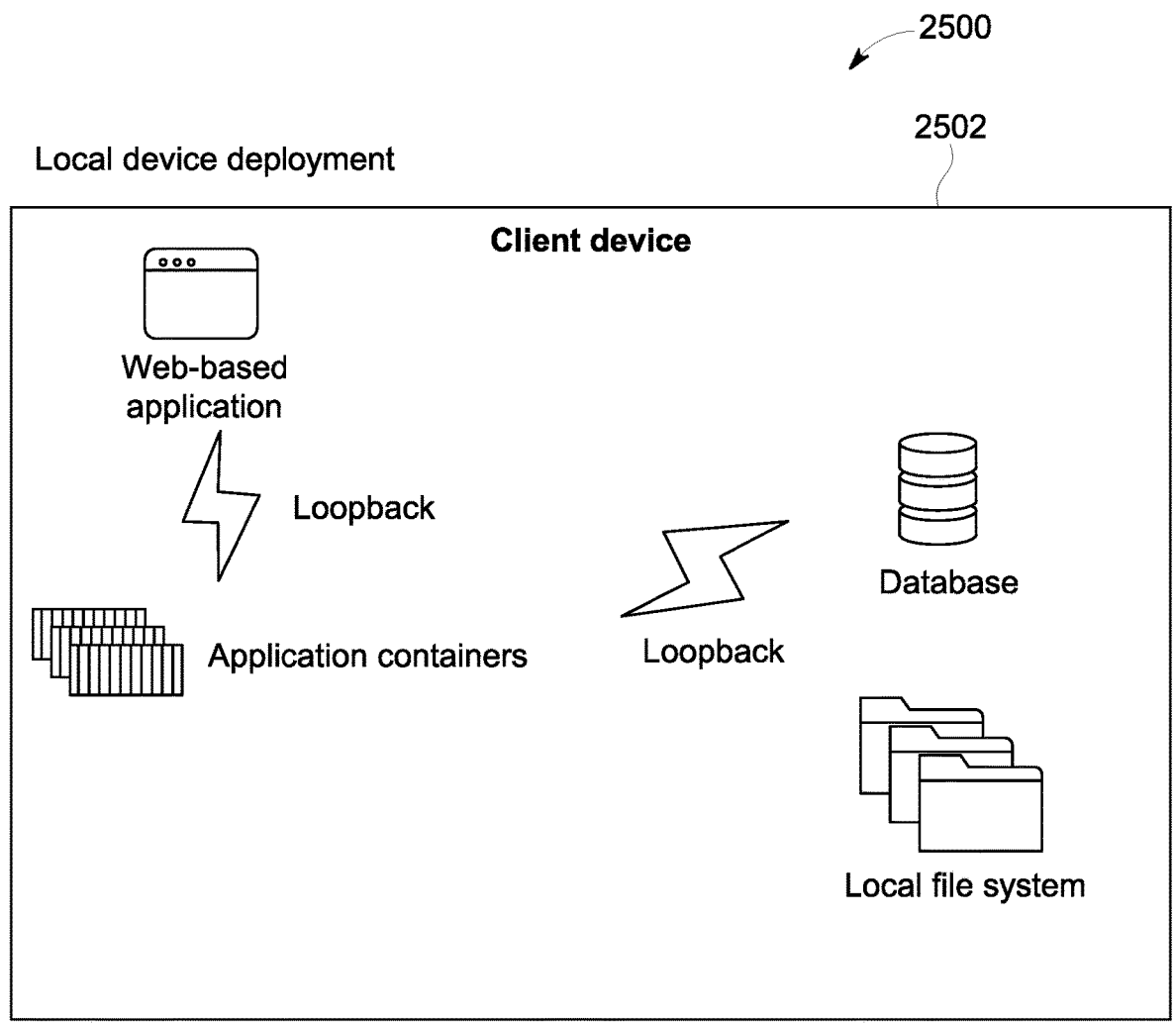
FIG. 18 shows a schematic block diagram of another sample-computing environment, according to an embodiment.

FIG. 18 illustrates a schematic block diagram of another example computing environment in accordance with this disclosure in which the subject systems, methods and computer readable media can be deployed. The computing environment includes a local device deployment in which all of the components of systems herein are provided at a single client device 2502. With this implementation, the client device 2502 can include a web-based application which can be communicatively coupled via a loopback to one or more application containers. The one or application containers can be communicatively coupled via a loopback to one or more databases and/or one or more local file systems.

Figure 19:
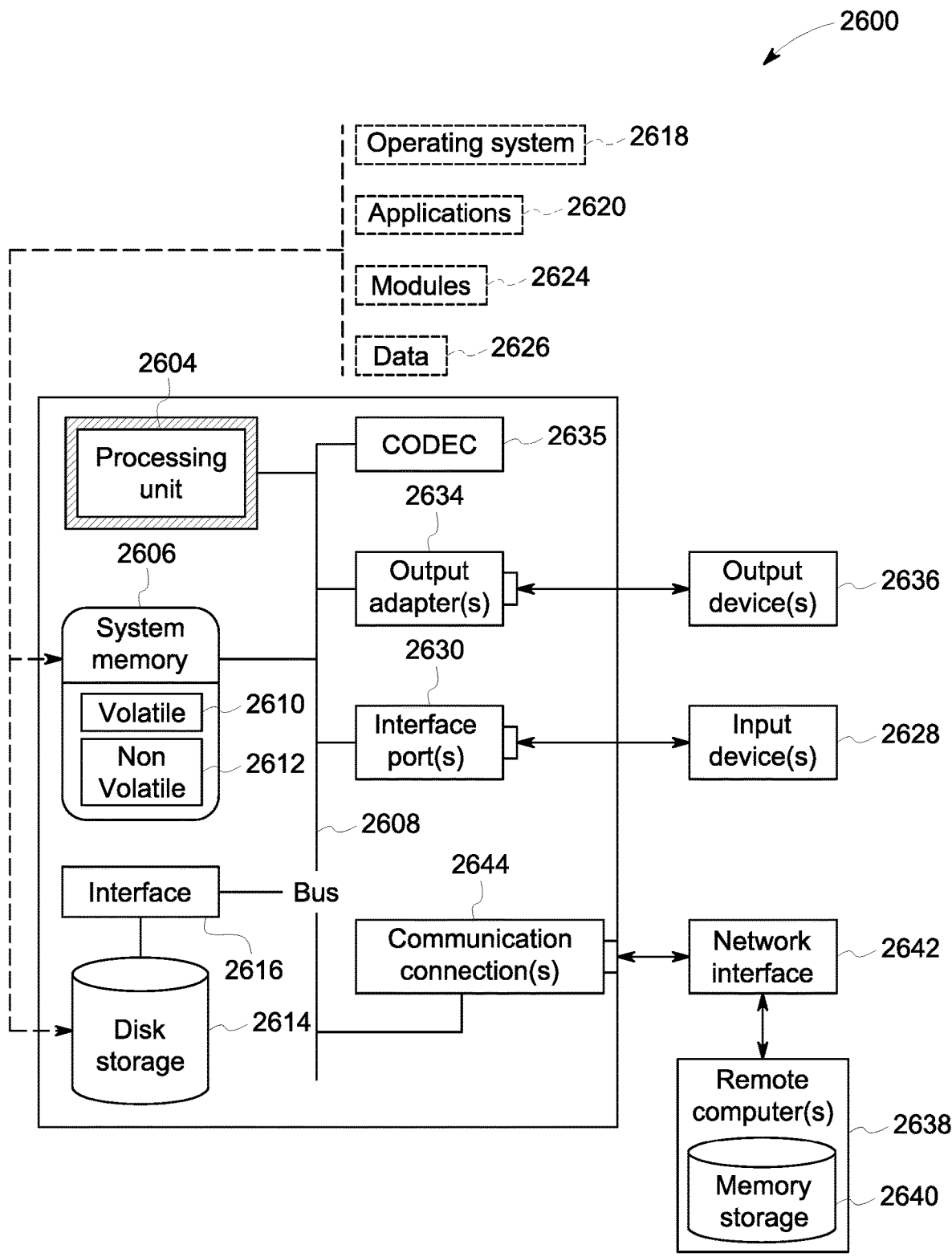
FIG. 19 shows a schematic block diagram illustrating a suitable operating environment, according to an embodiment.

With reference to FIG. 19, a suitable environment 2600 for implementing various aspects of the claimed subject matter includes a computer 2602. The computer 2602 includes a processing unit 2604, a system memory 2606, a codec 2605, and a system bus 2608. The system bus 2608 couples system components including, but not limited to, the system memory 2606 to the processing unit 2604. The processing unit 2604 can be any of various available processors. Dual microprocessors and other multiprocessor architectures also can be employed as the processing unit 2604.

The system bus 2608 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 22104), and Small Computer Systems Interface (SCSI).

The system memory 2606 includes volatile memory 2610 and non-volatile memory 2612. The basic input/output system (BIOS), containing the basic routines to transfer information between elements within the computer 2602, such as during start-up, is stored in non-volatile memory 2612. In addition, according to present innovations, codec 2605 may include at least one of an encoder or decoder, wherein the at least one of an encoder or decoder may consist of hardware, a combination of hardware and software, or software. Although, codec 2605 is depicted as a separate component, codec 2605 may be contained within non-volatile memory 2612. By way of illustration, and not limitation, non-volatile memory 2612 can include read only memory (ROM), programmable ROM (PROM), electrically programmable ROM (EPROM), electrically erasable programmable ROM (EEPROM), or flash memory. Volatile memory 2210 includes random access memory (RAM), which acts as external cache memory. According to present aspects, the volatile memory may store the write operation retry logic and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM).

Computer 2602 may also include removable/non-removable, volatile/non-volatile computer storage medium. FIG. 19 illustrates, for example, disk storage 2614. Disk storage 2614 includes, but is not limited to, devices like a magnetic disk drive, solid state disk (SSD) floppy disk drive, tape drive, Zip drive, flash memory card, or memory stick. In addition, disk storage 2614 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2614 to the system bus 2608, a removable or non-removable interface is typically used, such as interface 2616.

It is to be appreciated that FIG. 16 describes software that acts as an intermediary between users and the basic computer resources described in the suitable operating environment 2600. Such software includes an operating system 2618. Operating system 2618, which can be stored on disk storage 2614, acts to control and allocate resources of the computer system 2602. Applications 2620 take advantage of the management of resources by operating system 2618 through program modules 2624, and program data 2626, such as the boot/shutdown transaction table and the like, stored either in system memory 2606 or on disk storage 2614. It is to be appreciated that the claimed subject matter can be implemented with various operating systems or combinations of operating systems.

A user enters commands or information into the computer 2602 through input device(s) 2628. Input devices 2628 include, but are not limited to, a pointing device such as a mouse, trackball, stylus, touch pad, keyboard, microphone, joystick, game pad, satellite dish, scanner, TV tuner card, digital camera, digital video camera, web camera, microphone, and the like. These and other input devices connect to the processing unit 2604 through the system bus 2608 via interface port(s) 2630. Interface port(s) 2630 include, for example, a serial port, a parallel port, a game port, and a universal serial bus (USB). Output device(s) 2636 use some of the same type of ports as input device(s). Thus, for example, a USB port may be used to provide input to computer 2602, and to output information from computer 2602 to an output device 2636. Output adapter 2634 is provided to illustrate that there are some output devices 2636 like monitors, speakers, and printers, among other output devices 2636, which require special adapters. The output adapters 2634 include, by way of illustration and not limitation, video and sound cards that provide a means of connection between the output device 2636 and the system bus 2608. It should be noted that other devices and/or systems of devices provide both input and output capabilities such as remote computer(s) 2638.

Computer 2602 can operate in a networked environment using logical connections to one or more remote computers, such as remote computer(s) 2638. The remote computer(s) 2638 can be a personal computer, a server, a router, a network PC, a workstation, a microprocessor based appliance, a peer device, a smart phone, a tablet, or other network node, and typically includes many of the elements described relative to computer 2602. For purposes of brevity, only a memory storage device 2640 is illustrated with remote computer(s) 2638. Remote computer(s) 2638 is logically connected to computer 2602 through a network interface 2642 and then connected via communication connection(s) 2644. Network interface 2642 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2644 refers to the hardware/software employed to connect the network interface 2642 to the bus 2608. While communication connection 2644 is shown for illustrative clarity inside computer 2602, it can also be external to computer 2602. The hardware/software necessary for connection to the network interface 2642 includes, for exemplary purposes only, internal and external technologies such as, modems including regular telephone grade modems, cable modems and DSL modems, ISDN adapters, and wired and wireless Ethernet cards, hubs, and routers.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A communication engine embodied on a non-transitory computer readable storage medium storing one or more programs, the one or more programs comprising instructions, which when executed by one or more processors of an electronic device, cause the device to:
    monitor a task state of a user;
    receive an incoming matter;
    analyze the incoming matter with a classification model, wherein the classification model comprises a trained neural network;
    compare the analyzed incoming matter with a priority of the task state of the user; and
    interrupt the user by providing the incoming matter to the user if a priority of the analyzed incoming matter is greater than the priority of the task state of the user, and providing the incoming matter to a second user if the priority of the analyzed incoming matter is lower than the priority of the task state of the user, wherein the providing the incoming matter to the user comprises appending additional information based on output from the trained neural network;
    obtain sensor data indicating a pattern of user activity that identifies inputs into the electronic device from the user that co-occur, wherein the sensor data comprises machine data from an eye tracking sensor, a camera, a microphone, or a combination thereof, the sensor data representing a user's interaction with the electronic device, wherein the sensor data is obtained via a system bus connecting the eye tracking sensor, the camera, and the microphone to the one or more processors; and
    provide refocus output, based on the pattern of user activity identified using the sensor data, to a display screen of a computing device by executing a ready to resume process, wherein the refocus output comprises data to be provided to the user via the display screen of the computing device, wherein the refocus output is generated using computer executable instructions that perform artificial intelligence analysis using a saved context and the sensor data, an interruption type, and an escalation of the task state of the user in response to a patient status.

2. The communication engine embodied on a non-transitory computer readable storage medium of claim 1, wherein: if the priority of the task state of the user is greater than the priority of the incoming matter, the incoming matter is recorded and saved to be provided to the user at a future time.

3. The communication engine embodied on a non-transitory computer readable storage medium of claim 2, wherein:

the future time when the incoming matter is provided to the user is when the user has a lull in task activity as identified by an activity model.

4. The communication engine embodied on a non-transitory computer readable storage medium of claim 1, wherein the device is further caused to, after the compare step:
   determine as to whether the communication engine can provide an automated response to an originator of the incoming matter based on the output of the classification model;
   pull data from an information storage in response to the incoming matter;
   customize an output response based on one or more originator details and including the pulled data; and
   provide the output response to the originator of the incoming matter without user interruption.

5. The communication engine embodied on a non-transitory computer readable storage medium of claim 1, wherein the device is further caused to collect task performance metrics and outcomes and provides the task performance metrics and outcomes to a learning engine to improve the classification model and prioritization comparison.

6. The communication engine embodied on a non-transitory computer readable storage medium of claim 1, wherein the device is further caused to receive direct input from a user as to their preferences and feedback, and adjust the prioritization comparison in the future based on the direct input from a user.

7. The communication engine embodied on a non-transitory computer readable storage medium of claim 1, wherein the comparison of the analyzed incoming matter with the priority of the task state of the user also compares the incoming matter with a priority of the upcoming tasks of the user from a worklist manager for the user.

8. A method of operating a communication engine, comprising: at a device having one or more processors and memory:
   monitoring a task state of a user;
   receiving an incoming matter;
   analyzing the incoming matter with a classification model, wherein the classification model comprises a trained neural network;
   comparing the analyzed incoming matter with a priority of the task state of the user; and
   interrupting the user by providing the incoming matter to the user if a priority of the analyzed incoming matter is greater than the priority of the task state of the user, and providing the incoming matter to a second user if the priority of the analyzed incoming matter is lower than the priority of the task state of the user, wherein the providing the incoming matter to the user comprises appending additional information based on output from the trained neural network;
   obtaining sensor data indicating a pattern of user activity that identifies inputs into the electronic device from the user that co-occur, wherein the sensor data comprises machine data from an eye tracking sensor, a camera, a microphone, or a combination thereof, the sensor data representing a user's interaction with the electronic device, wherein the sensor data is obtained via a system bus connecting the eye tracking sensor, the camera, and the microphone to the one or more processors; and
   providing refocus output, based on the pattern of user activity identified using the sensor data, to a display screen of a computing device by executing a ready to resume process, wherein the refocus output comprises data to be provided to the user via the display screen of the computing device, wherein the refocus output is generated using computer executable instructions that perform artificial intelligence analysis using a saved context and the sensor data, an interruption type, and an escalation of the task state of the user in response to a patient status.

9. The method of claim 8, wherein: if the priority of the task state of the user is greater than the priority of the incoming matter, the incoming matter is recorded and saved to be provided to the user at a future time.

10. The method of claim 9, wherein: the future time when the incoming matter is provided to the user is when the user has a lull in task activity as identified by an activity model.

11. The method of claim 8, wherein after the comparing step,
   determining as to whether the communication engine can provide an automated response to an originator of the incoming matter based on the output of the classification model;
   pulling data from an information storage in response to the incoming matter;
   customizing an output response based on one or more originator details and including the pulled data; and
   providing the output response to the originator of the incoming matter without user interruption.

12. The method of claim 8, wherein the device is further caused to receive direct input from a user as to their preferences and feedback, and adjusts the prioritization comparison in the future based on the direct input from a user.

13. An electronic device, comprising:
   one or more processors;
   memory; and
   one or more programs, wherein the one or more programs are stored in the memory and configured to be executed by the one or more processors, the one or more programs including instructions for:
   monitoring a task state of a user;
   receiving an incoming matter;
   analyzing the incoming matter with a classification model, wherein the classification model comprises a trained neural network;
   comparing the analyzed incoming matter with a priority of the task state of the user; and
   interrupting the user by providing the incoming matter to the user if a priority of the analyzed incoming matter is greater than the priority of the task state of the user, and providing the incoming matter to a second user if the priority of the analyzed incoming matter is lower than the priority of the task state of the user, wherein the providing the incoming matter to the user comprises appending additional information based on output from the trained neural network;
   obtaining sensor data indicating a pattern of user activity that identifies inputs into the electronic device from the user that co-occur, wherein the sensor data comprises machine data from an eye tracking sensor, a camera, a microphone, or a combination thereof, the sensor data representing a user's interaction with the electronic device, wherein the sensor data is obtained via a system bus connecting the eye tracking sensor, the camera, and the microphone to the one or more processors; and
   providing refocus output, based on the pattern of user activity identified using the sensor data, to a display screen of a computing device by executing a ready to resume process, wherein the refocus output comprises data to be provided to the user via the display screen of the computing device, wherein the refocus output is generated using computer executable instructions that perform artificial intelligence analysis using a saved context and the sensor data. an interruption type, and an escalation of the task state of the user in response to a patient status.

14. The device of claim 13, wherein: if the priority of the task state of the user is greater than the priority of the incoming matter, the incoming matter is recorded and saved to be provided to the user at a future time.

15. The device of claim 14, wherein: the future time when the incoming matter is provided to the user is when the user has a lull in task activity as identified by an activity model.

16. The device of claim 13, wherein after the comparing step,
    determining as to whether the communication engine can provide an automated response to an originator of the incoming matter based on the output of the classification model;
    pulling data from an information storage in response to the incoming matter;
    customizing an output response based on one or more originator details and including the pulled data; and
    providing the output response to the originator of the incoming matter without user interruption.

17. The device of claim 13, wherein if the priority of the incoming matter is higher than the priority of the task state of the user and the user is interrupted by the incoming matter, method further comprises:
    saving the task state of the user;
    saving a task context of the user;
    preparing an output refocus communication for when the user resumes the interrupted task; and
    when the user resumes the interrupted task, providing the output refocus communication and automatically return the device software status to the task state of the user when the interruption occurred.

18. The device of claim 13, wherein the device is further caused to receive direct input from a user as to their preferences and feedback, and adjusts the prioritization comparison in the future based on the direct input from a user.

* * * * *